US011883825B2

(12) United States Patent
Salomon et al.

(10) Patent No.: US 11,883,825 B2
(45) Date of Patent: Jan. 30, 2024

(54) CARTRIDGE AND SYSTEM FOR ANALYZING BODY LIQUID

(71) Applicant: MeMed Diagnostics Ltd., Tirat HaCarmel (IL)

(72) Inventors: Noga Salomon, Haifa (IL); Kfir Oved, Hof HaCarmel (IL); Yana Khalfin, Haifa (IL); Omer Nahum Katzenelson, Atlit (IL); Amir Gelman, Kibbutz Nir-David (IL); Moran Brouk Rudich, M.P. Misgav (IL); Roy Navon, Tel-Aviv (IL); Assaf Cohen-Dotan, Natania (IL); Eran Eden, Haifa (IL); Salit Tzaban, Nofit (IL); Arnon Zangvil, Tel Aviv-Jaffa (IL); Ofer Halbreich, Tel-Aviv (IL); Matthew Fenwick, Mount Waverley (AU); Adrian Charles Ian Scott-Murphy, Surrey Hills (AU); Matthew Hou-Pou Yeung, Nunawading (AU); James William Luther, Milan (IT); Barbara Tornaghi, Monza (IT); Andrea Besana, Seveso (IT); Thomas Sanelli Crugnale, Lysterfield (AU)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 380 days.

(21) Appl. No.: 16/760,546

(22) PCT Filed: Sep. 2, 2018

(86) PCT No.: PCT/IL2018/050972
§ 371 (c)(1),
(2) Date: Apr. 30, 2020

(87) PCT Pub. No.: WO2019/087176
PCT Pub. Date: May 9, 2019

(65) Prior Publication Data
US 2020/0290037 A1    Sep. 17, 2020

Related U.S. Application Data

(60) Provisional application No. 62/694,083, filed on Jul. 5, 2018, provisional application No. 62/581,728, filed (Continued)

(51) Int. Cl.
*B01L 3/00* (2006.01)
*G01N 35/00* (2006.01)
(Continued)

(52) U.S. Cl.
CPC ...... *B01L 3/50853* (2013.01); *G01N 35/0098* (2013.01); *G01N 35/0099* (2013.01);
(Continued)

(58) Field of Classification Search
None
See application file for complete search history.

(56) References Cited

U.S. PATENT DOCUMENTS

D282,208 S    1/1986 Lowry
4,576,185 A   3/1986 Proud et al.
(Continued)

FOREIGN PATENT DOCUMENTS

CN    101093639    12/2007
CN    101098956    5/2012
(Continued)

OTHER PUBLICATIONS

Ex Parte Quayle OA dated Jan. 10, 2020 From the US Patent and Trademark Office Re. U.S. Appl. No. 29/645,126. (10 pages).
(Continued)

*Primary Examiner* — Brian R Gordon

(57) ABSTRACT

In a cartridge device for analyzing a body liquid, a first member of the cartridge has two or more wells for perform-
(Continued)

ing assays, and a second member of the cartridge has a compartment for holding one or more disposable pipette tips.

10 Claims, 23 Drawing Sheets

Related U.S. Application Data on Nov. 5, 2017, provisional application No. 62/580,496, filed on Nov. 2, 2017.

(51) Int. Cl.
*G01N 35/10* (2006.01)
*A61B 5/15* (2006.01)

(52) U.S. Cl.
CPC ........ *G01N 35/10* (2013.01); *A61B 5/150022* (2013.01); *B01L 2300/044* (2013.01); *B01L 2400/06* (2013.01); *G01N 2035/00851* (2013.01); *G01N 2035/103* (2013.01)

(56) References Cited

U.S. PATENT DOCUMENTS

| | | | |
|---|---|---|---|
| 5,568,881 A * | 10/1996 | Chi .................. | B01L 9/543 221/175 |
| 5,681,743 A * | 10/1997 | Brian .................. | B01L 3/5085 222/499 |
| D438,633 S | 3/2001 | Miller | |
| 6,254,826 B1 * | 7/2001 | Acosta .................. | B01L 3/0275 422/65 |
| 7,157,047 B2 | 1/2007 | Tajima | |
| 7,473,396 B2 | 1/2009 | Tajima | |
| D631,554 S | 1/2011 | Jackson et al. | |
| D638,953 S | 5/2011 | Cavada et al. | |
| D639,975 S | 6/2011 | Doyle et al. | |
| D649,658 S | 11/2011 | Belfance et al. | |
| 8,142,737 B2 | 3/2012 | Tajima | |
| 8,211,386 B2 | 7/2012 | Talmer et al. | |
| D669,169 S | 10/2012 | Washington et al. | |
| 8,333,930 B2 | 12/2012 | Hanafusa et al. | |
| 8,383,421 B2 | 2/2013 | Yanagida et al. | |
| 8,409,872 B2 | 4/2013 | Yokoi et al. | |
| D682,441 S | 5/2013 | Kim | |
| D686,311 S | 7/2013 | Mori | |
| 8,476,080 B2 | 7/2013 | Talmer et al. | |
| 8,697,377 B2 | 4/2014 | Burd et al. | |
| D704,348 S | 5/2014 | Shibata et al. | |
| D707,825 S | 6/2014 | Murai | |
| D718,462 S | 11/2014 | Cook et al. | |
| 9,335,339 B2 | 5/2016 | Tajima | |
| 9,446,406 B2 | 9/2016 | Gordon et al. | |
| D774,205 S | 12/2016 | Grace et al. | |
| D785,811 S | 5/2017 | Watts et al. | |
| 9,857,384 B2 * | 1/2018 | Ørning .................. | B01L 3/02 |
| D818,146 S | 5/2018 | Tanaka | |
| D821,601 S | 6/2018 | Henderson | |
| D827,859 S | 9/2018 | Mathers et al. | |
| D830,548 S | 10/2018 | Kemp | |
| D833,639 S | 11/2018 | Peltosaari et al. | |
| 10,118,177 B2 | 11/2018 | Burroughs et al. | |
| D843,009 S | 3/2019 | Watts et al. | |
| D853,873 S | 7/2019 | Schueren et al. | |
| D854,703 S | 7/2019 | Juhlin et al. | |
| 2005/0133512 A1 * | 6/2005 | Prokopp .................. | B65D 25/108 220/601 |
| 2010/0166616 A1 * | 7/2010 | Price .................. | B01L 9/543 422/400 |
| 2011/0226643 A1 * | 9/2011 | Kates .................. | B65D 51/20 53/471 |
| 2012/0149035 A1 | 6/2012 | Burd et al. | |
| 2012/0227471 A1 | 9/2012 | Smith et al. | |
| 2013/0116597 A1 * | 5/2013 | Rudge .................. | A61B 5/150358 436/63 |
| 2013/0183769 A1 * | 7/2013 | Tajima .................. | G01N 21/03 422/82.05 |
| 2013/0287651 A1 | 10/2013 | Talmer et al. | |
| 2014/0017712 A1 | 1/2014 | Shoji et al. | |
| 2014/0284338 A1 * | 9/2014 | Jordan .................. | B65D 47/00 220/780 |
| 2014/0302611 A1 * | 10/2014 | Orning .................. | G01N 33/92 436/71 |
| 2014/0378348 A1 * | 12/2014 | Makarewicz, Jr. .................. B01L 3/502715 506/40 |
| 2015/0250456 A1 | 9/2015 | Olgun | |
| 2016/0051415 A1 | 2/2016 | Kuan et al. | |
| 2017/0065971 A1 | 3/2017 | Kreifels et al. | |
| 2017/0350838 A1 | 12/2017 | Katsumoto et al. | |
| 2019/0299217 A1 * | 10/2019 | Motadel .................. | B01L 9/543 |
| 2021/0205817 A1 * | 7/2021 | Bonnoitt, Jr. .................. | B01L 9/543 |

FOREIGN PATENT DOCUMENTS

| | | |
|---|---|---|
| CN | 102768826 | 11/2012 |
| CN | 103946687 | 7/2014 |
| CN | 107978280 | 5/2018 |
| CN | 108227287 | 6/2018 |
| CN | 108694914 | 10/2018 |
| CN | 109192150 | 1/2019 |
| CN | 109686320 | 4/2019 |
| CN | 109785800 | 5/2019 |
| CN | 110349532 | 10/2019 |
| CN | 111028767 | 4/2020 |
| CN | 111354319 | 6/2020 |
| CN | 111580304 | 8/2020 |
| CN | 112331151 | 2/2021 |
| EP | 2484748 | 12/2022 |
| JP | 2004-531725 | 10/2004 |
| JP | 2007-178328 | 7/2007 |
| JP | 2014-528577 | 10/2014 |
| JP | 2014-211437 | 11/2014 |
| KR | 10-2004-0012811 | 2/2004 |
| KR | 10-0837335 | 6/2008 |
| TW | 558699 | 10/2003 |
| WO | WO 01/11374 | 2/2001 |
| WO | WO 02/090995 | 11/2002 |
| WO | WO 2004/061418 | 7/2004 |
| WO | WO 2011/040504 | 2/2013 |
| WO | WO 2013/043203 | 3/2013 |
| WO | WO 2013/049706 | 4/2013 |
| WO | WO 2013/068760 | 5/2013 |
| WO | WO 2019/087176 | 5/2019 |

OTHER PUBLICATIONS

International Preliminary Report on Patentability dated May 14, 2020 From the International Bureau of WIPO Re. Application No. PCT/IL2018/050972. (10 Pages).
Official Action dated Sep. 20, 2019 From the US Patent and Trademark Office Re. U.S. Appl. No. 29/645,126. (19 pages).
Official Action dated Nov. 26, 2019 From the US Patent and Trademark Office Re. U.S. Appl. No. 29/662,120. (13 pages).
Restriction Official Action dated Feb. 13, 2020 From theUS Patent and Trademark Office Re. U.S. Appl. No. 29/662,119. (12 pages).
MeMed "The platform: MeMed Key TM", retrieved from me-med.com, 3 Pages, 2018.
Examination Report Under Sections 12 & 13 of the Patents Act, 1970 and the Patents Rules, 2003 dated Mar. 23, 2022 From the Government of India, Intellectual Property India, Patents, Designs, Trade Marks, Geographical Indications, The Patent Office Re. Application No. 202037022566. (8 Pages).
Official Action Dated Jun. 24, 2020 from the US Patent and Trademark Office Re. U.S. Appl. No. 29/662,119. (18 pages).
Patent Examination Report Dated Feb. 14, 2022 From the Australian Government, IP Australia Re. Application No. 2018362024 with Claims. (7 Pages).

(56) References Cited

OTHER PUBLICATIONS

Supplementary European Search Report and the European Search Opinion dated Jul. 8, 2021 From the European Patent Office Re. Application No. 18874575.6. (50 Pages).
Official Action dated May 27, 2021 from the US Patent and Trademark Office Re. U.S. Appl. No. 29/662,119. (8 pages).
Notice of Allowance dated Feb. 25, 2022 from US Patent and Trademark Office Re. U.S. Appl. No. 29/662,119. (6 pages).
Official Action dated Nov. 3, 2021 from US Patent and Trademark Office Re. U.S. Appl. No. 29/662,119. (8 pages).
Official Action dated Dec. 8, 2020 from the US Patent and Trademark Office Re. U.S. Appl. No. 29/662,119. (10 pages).
International Search Report and the Written Opinion Dated Dec. 26, 2018 From the International Searching Authority Re. Application No. PCT/IL2018/050972. (30 Pages).
Notice of Reasons for Rejection dated Oct. 18, 2022 From the Japan Patent Office Re. Application No. 2020-524089 and Its Translation Into English. (13 Pages).
Office Action dated Oct. 26, 2022 From the Israel Patent Office Re. Application No. 274377. (4 Pages).
Decision on Rejection dated Jul. 10, 2023 From the State Intellectual Property Office of the People's Republic of China Re. Application No. 201880078086.6. (8 Pages).
English Summary dated Jul. 21, 2023 of Decision on Rejection dated Jul. 10, 2023 From the State Intellectual Property Office of the People's Republic of China Re. Application No. 201880078086.6. (1 page).
Grounds of Reason of Rejection dated Jun. 7, 2023 From the Korean Intellectual Property Office Re. Application No. 10-2020-7015821. (9 Pages).
Notice of Reason(s) for Rejection dated Jun. 13, 2023 From the Japan Patent Office Re. Application No. 2020-524089 and Its Translation Into English. (4 Pages).
Requisition by the Examiner dated May 26, 2023 From the Innovation, Science and Economic Development Canada, Canadian Intellectual Property Office Rc. Application No. 3,079,954. (4 pages).
Translation dated Jun. 22, 2023 of Grounds of Reason of Rejection dated Jun. 7, 2023 From the Korean Intellectual Property Office Re. Application No. 10-2020-7015821. (11 Pages).
Machine Translation dated Aug. 17, 2023 of Notification of Office Action dated Feb. 23, 2023 From the State Intellectual Property Office of the People's Republic of China Re. Application No. 201880078086.6 (7 Pages).
Notification of Office Action and Search Report dated Aug. 31, 2022 From the State Intellectual Property Office of the People's Republic of China Re. Application No. 201880078086.6 and Its Summary of the Office Action in English. (11 Pages).
Notification of Office Action dated Feb. 23, 2023 From the State Intellectual Property Office of the People's Republic of China Re. Application No. 201880078086.6 and it's English Summary. (9 Pages).
Translation Dated Aug. 14, 2023 of Decision on Rejection dated Jul. 10, 2023 From the State Intellectual Property Office of the People's Republic of China Re. Application No. 201880078086.6. (7 pages).
Translation dated Aug. 17, 2023 of Notification of Office Action and Search Report dated Aug. 31, 2022 From the State Intellectual Property Office of the People's Republic of China Re. Application No. 201880078086.6. (11 Pages).

\* cited by examiner

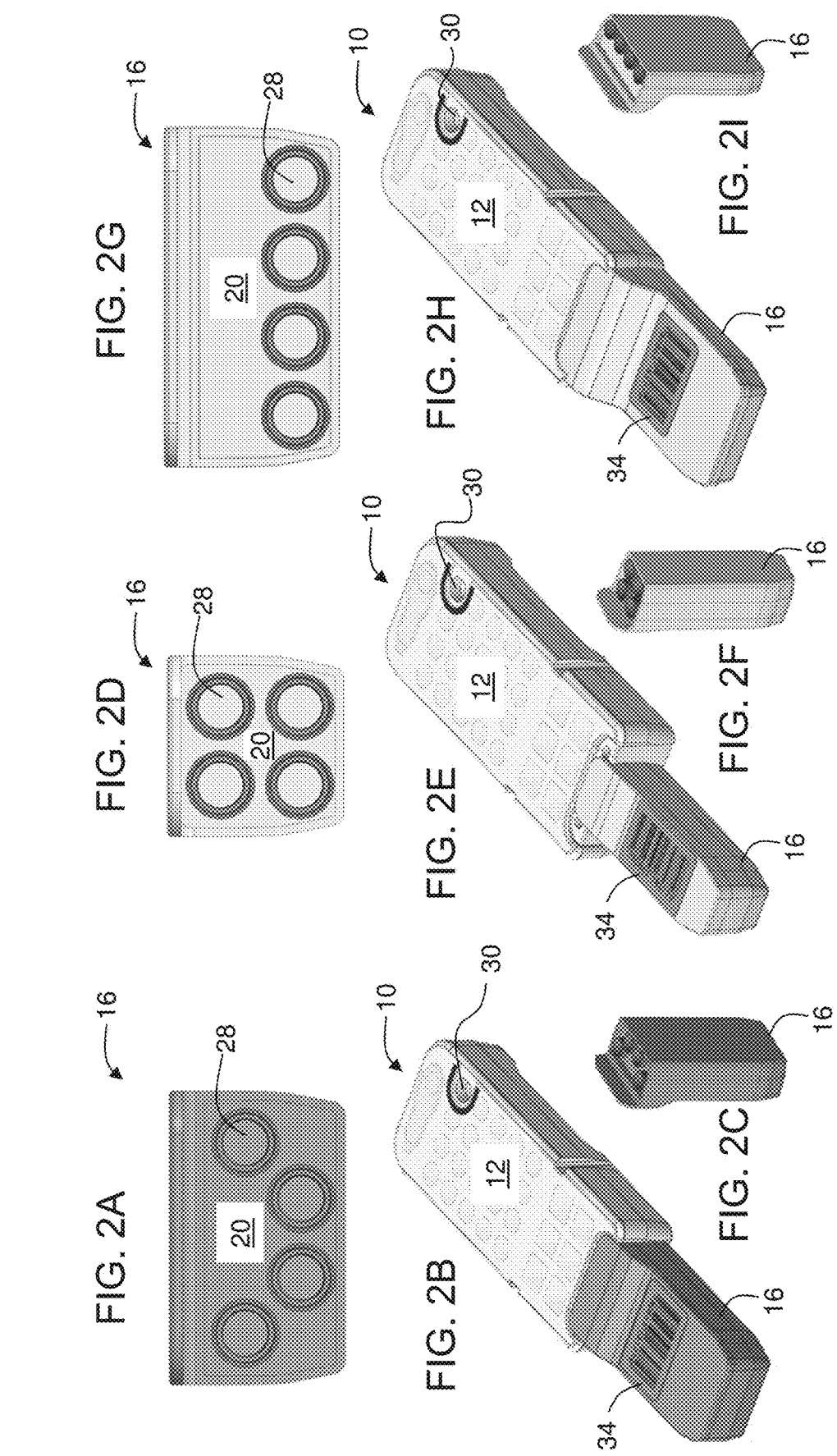

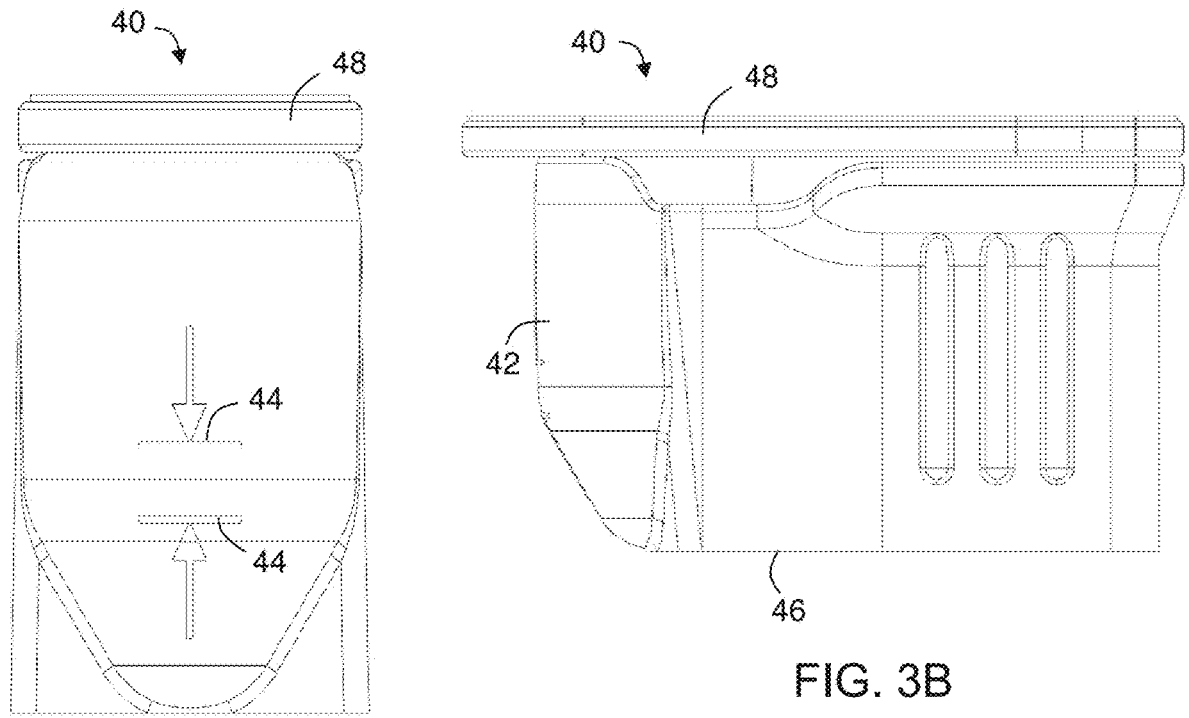
FIG. 3A
FIG. 3B
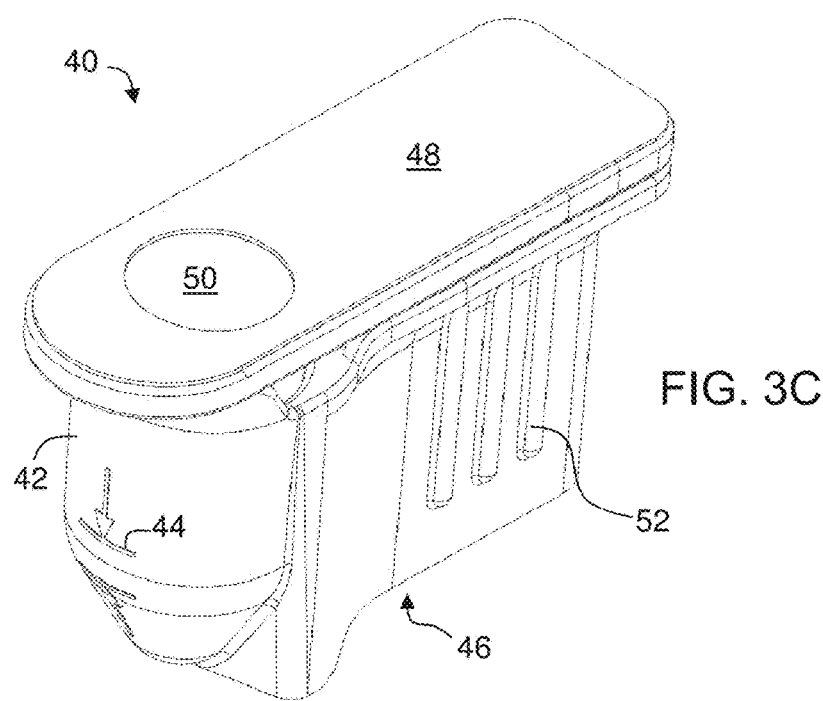
FIG. 3C

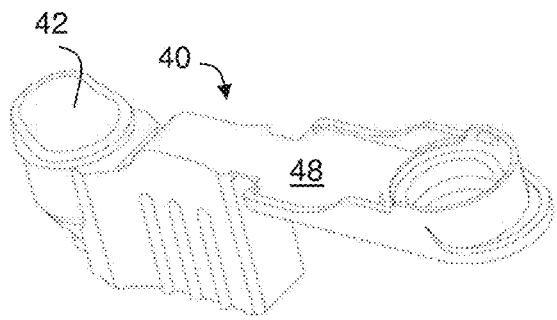
FIG. 3D
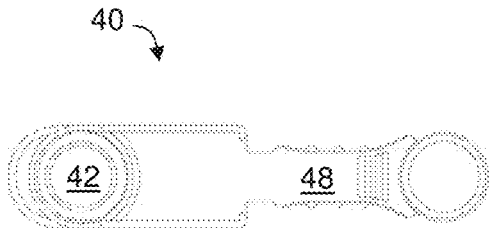
FIG. 3E
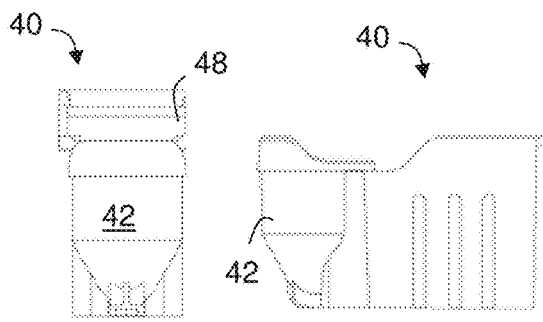
FIG. 3F
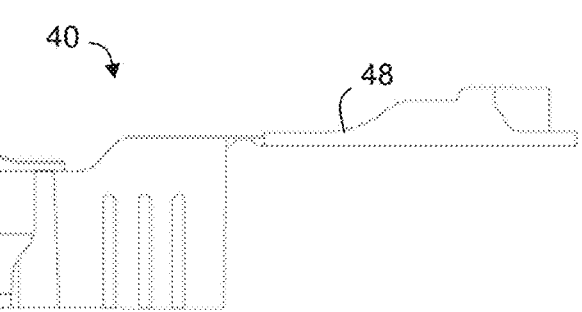
FIG. 3G
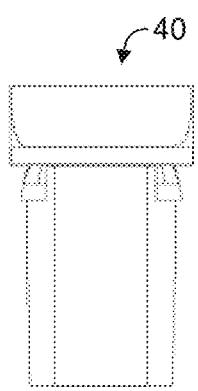
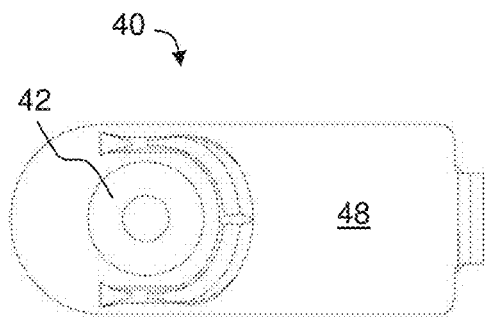
FIG. 3H   FIG. 3I
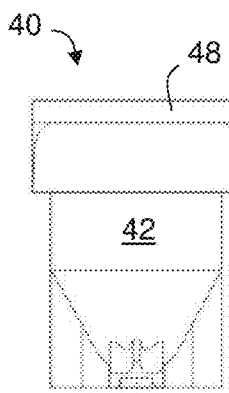
FIG. 3J
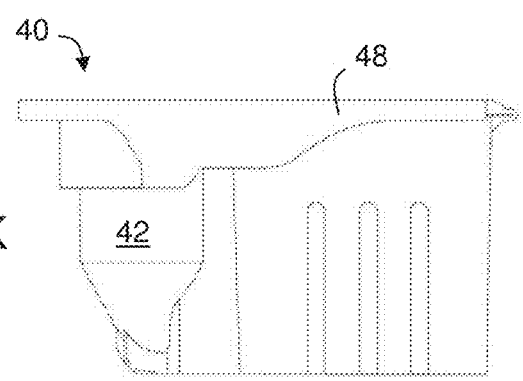
FIG. 3K

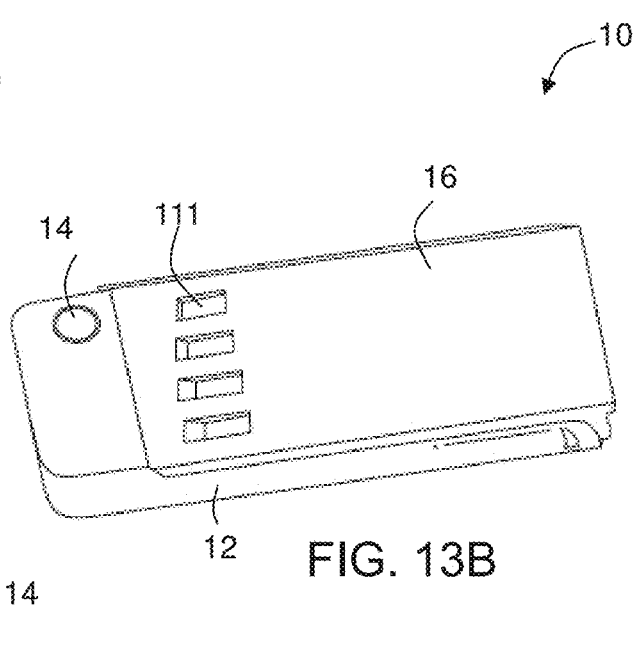
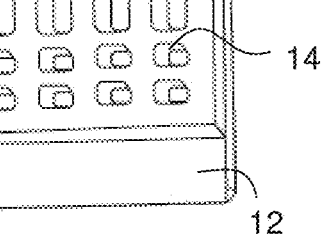
FIG. 13A
FIG. 13B

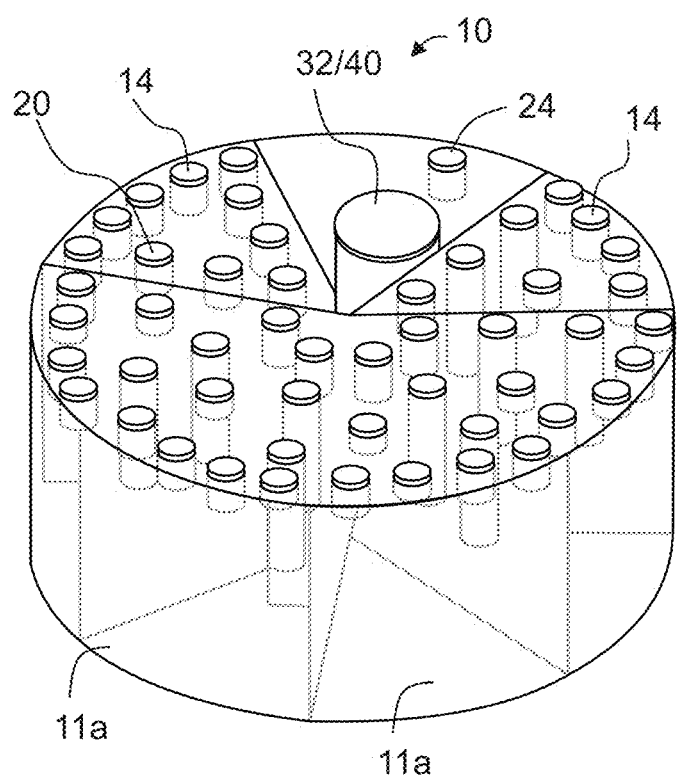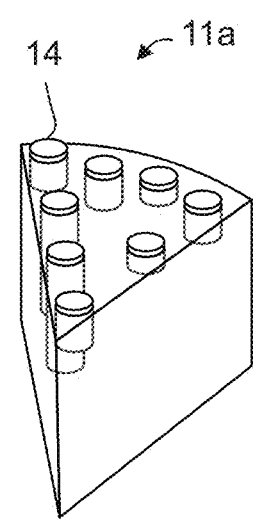
FIG. 15A
FIG. 15B

CARTRIDGE AND SYSTEM FOR ANALYZING BODY LIQUID

RELATED APPLICATIONS

This application is a National Phase of PCT Patent Application No. PCT/IL2018/050972 having International filing date of Sep. 2, 2018, which claims the benefit of priority under 35 USC § 119(e) of U.S. Provisional Patent Application Nos. 62/694,083 filed on Jul. 5, 2018, 62/581,728 filed on Nov. 5, 2017 and 62/580,496 filed on Nov. 2, 2017. The contents of the above applications are all incorporated by reference as if fully set forth herein in their entirety.

STATEMENT REGARDING FEDERALLY SPONSORED RESEARCH OR DEVELOPMENT

This invention was made with government support under contract number HDTRA1-17-C-0011 awarded by the Defense Threat Reduction Agency and grant number W81XWH-17-1-0694 awarded by the U.S. Army Medical Research Acquisition Activity. The government has certain rights in the invention.

FIELD AND BACKGROUND OF THE INVENTION

The present invention, in some embodiments thereof, relates to a medical device and, more particularly, but not exclusively, to a cartridge and system for analyzing a sample of body liquid, such as, but not limited to, blood.

The discovery of a vast number of disease biomarkers and the establishment of miniaturized medical systems facilitates the prediction, diagnosis and/or monitoring of treatment of diseases in a point-of-care (POC) setting. Point-of-care systems can rapidly deliver test results to medical personnel, other medical professionals and patients. Early diagnosis of a disease or disease progression can allow medical personnel to begin or modify therapy in a timely manner.

Multiplexed biomarker measurement can provide additional knowledge of the condition of a patient. For example, when monitoring the effects of a drug, three or more biomarkers can be measured in parallel. Typically, microtiter plates and other similar apparatuses have been used to perform multiplexed separation-based assays. A microtiter plate can perform a large number of assays in parallel.

U.S. Pat. No. 8,409,872 discloses a cartridge having two or more lines of well groups arranged in parallel, wherein each well group comprises a diluting well, and a reaction well in which a component in the sample reacts with a substance. A diluting solution is filled in the diluting well of each well group, and the cartridge is then sealed. The cartridge seal is pierced and the sample is dispensed in the diluting well of each well group to dilute the sample. The component in the diluted sample is reacted with the substance, and the amount of the reaction product is measured.

Additional background art includes U.S. Published Application Nos. 20130287651 and 20140017712, and U.S. Pat. Nos. 7,157,047, 7,473,396, 8,142,737, 8,211,386, 8,333,930, 8,383,421, 8,476,080, 8,697,377, 9,335,339, 9,446,406.

SUMMARY OF THE INVENTION

According to an aspect of some embodiments of the present invention there is provided a cartridge device for analyzing a liquid, such as, but not limited to, a body liquid. The cartridge comprises a first member having a plurality of wells for performing assays; and a second member, connected to the first member, and having a compartment for holding at least one disposable pipette tip in a generally upright orientation.

While the embodiments below are described with a particular emphasis to body liquid, it is to be understood that the device, kit, system and method described herein can be also employed in some embodiments of the present invention for analyzing other types of liquids, such as, but not limited to, liquid from river, sewage, water reservoir, food product and the like.

According to some embodiments of the invention, the second member is hingedly connected to the first member.

According to some embodiments of the invention, the second member is slideably connected to the first member.

Optionally, the first and second members are not connected to each other and are loaded separately into a system that analyzes the liquid.

According to some embodiments of the invention, the second member is oriented for holding the disposable pipette tip(s) in a generally upright orientation.

According to an aspect of some embodiments of the present invention there is provided a kit for analyzing a liquid (e.g., body liquid). The kit comprises a first member having a plurality of wells for performing assays; and a second member, connectable to the first member, and having a compartment for holding at least one disposable pipette tip.

According to an aspect of some embodiments of the present invention there is provided a cartridge device for analyzing liquid (e.g., body liquid). The cartridge device comprises a first plurality of wells, each having a tapered base; and a second plurality of wells. The two pluralities of wells are formed in a monolithic structure. At least some of the wells of the first plurality of wells contain a reagent therein. In some embodiments of the present invention one or more of the wells of the first plurality of wells is empty. One or more of the wells of the second plurality of wells is empty. In use, one or more of the empty wells of the second plurality of wells is optionally and preferably filed with a liquid to be analyzed, such as, but not limited to, a body liquid. Optionally, one or more of the wells of the second plurality of wells contain a reagent therein.

According to some embodiments of the invention the device comprises a covering structure covering the wells, the covering structure being selected from the group consisting of a pierceable foil, a non-flexible openable lid, a flexible openable lid, a one way valve, a labyrinth structure.

According to some embodiments of the invention, some of the wells are open and are not covered by a foil.

According to some embodiments of the invention the bottom of at least some the wells are shaped in a general conic shape.

According to some embodiments of the invention the bottom of at least some the wells are shaped in a generally spheric, round shape.

According to some embodiments of the bottom shape of the wells is spheric-round for some of the wells and conic for some other wells.

According to some embodiments of the invention, the device comprises a waste collecting chamber.

According to some embodiments of the invention, the waste collecting chamber is covered by a structure selected from the group consisting of a pierceable foil, a non-flexible openable lid, a flexible openable lid, and a one way valve.

According to some embodiments of the invention, the waste collecting chamber comprises a moisture absorber.

According to some embodiments of the invention, the waste collecting chamber is covered by a lid connected to or being an extension of the second member, to be exposed when the second member is hinged in a generally upright orientation.

According to some embodiments of the invention, the waste collecting chamber is covered by a foil, which is pierced to expose a waste collecting chamber before deposing waste to it.

According to some embodiments of the invention the waste collecting chamber is comprised of multiple chambers, each is a single use chamber, to which there is a single deposing of waste.

According to some embodiments of the invention, the waste collecting chamber is comprised on one chamber, with several entrance points.

According to some embodiments of the invention, the waste collecting chamber sealing foil is capable of being pierced several times in the same location According to some embodiments of the invention, the waste collecting chamber sealing foil is covered by a label.

According to some embodiments of the invention, the waste collecting chamber covering label is scored along a pattern to form a frangible piercing location defined by the pattern.

According to some embodiments of the invention, there is a plurality of frangible piercing locations, defined by a respective plurality of scored patterns.

According to some embodiments of the invention, at least two adjacent scored patterns are separated from each other. According to some embodiments of the invention, any two adjacent scored patterns are separated from each other According to some embodiments of the invention, at least one scored pattern has a shape of a cross. According to some embodiments of the invention, the cross is a right angle cross, e.g., shape of a plus symbol. According to some embodiments of the invention, the cross is acute angle cross, e.g., shape of an X symbol.

According to some embodiments of the invention, at least two adjacent scored pattern have shapes of differently oriented crosses or differently shaped crosses, to ensure that said scored patterns are separated from each other.

According to some embodiments of the invention, the scored patterns comprise right angle crosses, e.g., shape of plus symbols, and acute angle crosses, e.g., shape of X symbols, arranged in alternating manner.

According to some embodiments of the invention, the waste collecting chamber extends to beneath the wells.

According to some embodiments of the invention the waste collecting chamber is part of the first member.

According to some embodiments of the invention, the waste collecting chamber is part of the second member.

According to some embodiments of the invention, the device comprises a first waste collecting chamber, which is part of the first member, and a second waste collecting chamber, which is part of the second member.

According to some embodiments of the invention the second member is partitioned into a plurality of partitions, each constituted for holding one pipette tip.

According to some embodiments of the invention, the partitions are not isolated from each other.

According to some embodiments of the invention, the partitions are isolated from each other.

According to some embodiments of the invention, a number of the partitions equals at least a number of the assays.

According to some embodiments of the invention the wells comprise at least one well containing a first antibody immobilized on a solid magnetic carrier, and at least one well containing a second antibody labeled with labeling substance, and wherein the antibodies are selected to specifically bind to a target substance in the liquid (e.g., body liquid).

According to some embodiments of the invention, the labeling substance is an enzyme, and wherein the antibodies and the enzyme are selected for detecting the target substance by a sandwich ELISA test.

According to some embodiments of the invention, the antibodies are selected to specifically bind to a protein selected from the group consisting of TRAIL protein, CRP protein and IP-10 protein.

According to some embodiments of the invention, the device comprises the disposable pipette tip within the compartment.

According to some embodiments of the invention, the first member comprises a cavity constituted for receiving and fittedly holding a container containing the liquid (e.g., body liquid).

According to some embodiments of the invention, the cartridge device has a shape defined by a polygonal cross-section along a horizontal plane. According to some embodiments of the invention, the cartridge device has a shape of a cuboid.

According to some embodiments of the invention, the cartridge device has a shape defined by a round cross-section along a horizontal plane. According to some embodiments of the invention, the cartridge device has a shape of cylinder or a cylindrical sector.

According to some embodiments of the invention, the cartridge device has a plurality of connectable modular elements each constituted for performing a different assay. According to some embodiments of the invention each modular element having a respective portion of the first and second members, and constituted for performing a different assay. According to some embodiments of the invention, at least one modular element has a respective portion of the first member, and one modular element serves as the second member.

According to an aspect of some embodiments of the present invention there is provided a kit for analyzing a liquid (e.g., body liquid), the kit comprising, in separate packaging, the cartridge device and the container.

According to some embodiments of the invention, the container has a volume of from about 5 µl to about 500 µl or from about 50 µl to about 350 µl or from about 100 µl to about 300 µl.

According to some embodiments of the invention, the container has a flat base.

According to some embodiments of the invention, the container comprises a lid. According to some embodiments of the invention, the lid is a foldable lid. According to some embodiments of the invention, the lid is pierceable. According to some embodiments of the invention, the lid is pierceable and foldable. According to some embodiments of the invention, the lid is hingedly connected to the container. According to some embodiments of the invention, the lid is pierceable and hingedly connected to the container.

According to some embodiments of the invention, the container is transparent to visible light.

According to some embodiments of the invention, an inner wall of the container is at least partially coated with an anticoagulant.

According to an aspect of some embodiments of the present invention there is provided a system for analyzing a liquid such as, but not limited to, a body liquid. The system comprises: a cartridge holder, adapted for receiving the cartridge device and having a lever system for automatically hinging the second member responsively to the receiving. The system further comprises an internal analyzer system, having an analysis chamber and being configured for analyzing the liquid (e.g., body liquid) when enclosed in the analysis chamber. The system further comprises a robotic arm system carrying a pipette; and a controller configured for controlling the robotic arm system to establish a relative motion between the cartridge device and the pipette such that the pipette sequentially visits at least the cartridge device, the analysis chamber, and the compartment, and releases a tip of the pipette into the compartment.

According to an aspect of some embodiments of the present invention there is provided a system for analyzing a liquid (e.g., body liquid). The system comprises a first cartridge holder, adapted for receiving a first cartridge member having a plurality of wells for performing assays; and a second cartridge holder, adapted for receiving a second cartridge member having a compartment for holding at least one disposable pipette tip, wherein the first and second cartridge holders are optionally and preferably separated from each other. The system can further comprise an internal analyzer system having an analysis chamber, and being configured for analyzing the liquid (e.g., body liquid) when enclosed in the analysis chamber, and a robotic arm system carrying a pipette. The system can further comprise a controller configured for controlling the robotic arm system to establish a relative motion between the cartridge members and the pipette such that the pipette visits at least the tip compartment, picks up a tip from the compartment, visits the wells, the analysis chamber, and releases a tip of the pipette back into the compartment.

According to some embodiments of the system has dimensions of Xcm×Ycm×Zcm, wherein each of X, Y and Z is from about 75 to about 125, e.g., about 100. According to some embodiments of the system has dimensions of Xcm×Ycm×Zcm, wherein each of X, Y and Z is from about 35 to about 65, e.g., about 50. According to some embodiments of the system has dimensions of Xcm×Ycm×Zcm, wherein each of X, Y and Z is from about 16 to about 30, e.g., about 23. According to some embodiments of the system has dimensions of Xcm×Ycm×Zcm, wherein each of X and Y is from about 20 to about 26, e.g., about 23, and wherein Z is from about 26 to about 34, e.g., about 30.

According to some embodiments of the invention, the cartridge device comprises a pierceable film covering the wells, and the controller is configured for controlling the robotic arm system to pierce the film while visiting the cartridge device.

According to some embodiments of the invention, the cartridge device comprises a waste collecting chamber, wherein the controller is configured for controlling the robotic arm system to visit the waste collecting chamber after visiting the analysis chamber.

According to some embodiments of the invention, the second member is partitioned into a plurality of partitions, and the controller is configured for controlling the robotic arm system to release different pipette tips into different partitions.

According to some embodiments of the invention the first member comprises a cavity constituted for receiving and fittedly holding a container containing the liquid (e.g., body liquid), wherein the controller is configured for controlling the robotic arm system to visit the container.

According to some embodiments of the invention the wells comprise at least one well containing a first antibody immobilized on a solid magnetic carrier, and at least one well containing a second antibody labeled with labeling substance, wherein the antibodies are selected to specifically bind to a target substance in the liquid (e.g., body liquid), wherein the a controller is configured for establishing the relative motion such that the pipette aspirates the liquid (e.g., body liquid), the immobilized first antibody and the labeled second antibody into the tip, and wherein the system comprises a magnetic system constituted for separating the solid magnetic carrier, thereby also the target substance, from other components in the tip.

According to some embodiments of the invention, the system comprises a heating system.

According to some embodiments of the invention, the heating system comprises a stage configured to automatically engage the cartridge device from below responsively to the receiving of the cartridge device.

According to some embodiments of the invention, the heating system is configured to heat the cartridge by conduction.

According to some embodiments of the invention, the heating system is configured to heat the cartridge device by radiation or convection but without conduction.

According to some embodiments of the invention, the analysis chamber is a dark chamber and the analyzer system is an optical analyzer configured for detecting chemiluminescent signals from the pipette tip when the pipette tip is in the dark chamber.

According to some embodiments of the invention, an inner wall of the dark chamber is at least partially coated by a reflective coating.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-I are schematic illustrations of non-limiting examples for arrangements of partitions within a member of the device shown in FIGS. 1A-D, according to some embodiments of the present invention;

FIGS. 3A-K are schematic illustrations of a container suitable for being loaded into a cavity of the device shown in FIGS. 1A-I, according to some embodiments of the present invention;

FIGS. 13A and 13B are schematic illustrations of a cartridge device having a first member and a second member that is slideably connected to the first member, according to some embodiments of the present invention.

FIGS. 15A and 15B are schematic illustrations of a cartridge device in embodiments of the present invention in which the device has a shape of cylinder.

DESCRIPTION OF SPECIFIC EMBODIMENTS OF THE INVENTION

Figure 1A:
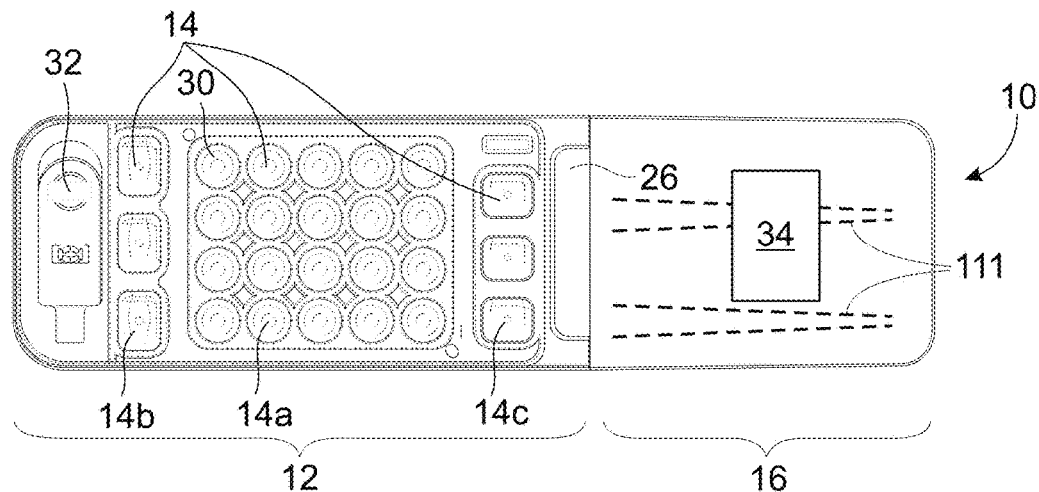
FIGS. 1A-I are schematic illustrations of a top view (FIG. 1A) a side view (FIGS. 1B, 1H and 1I) and perspective views (FIGS. 1C and 1D-G) of a cartridge device having a first member and a second member, according to some embodiments of the present invention.

The present invention, in some embodiments thereof, relates to a medical device and, more particularly, but not exclusively, to a cartridge and system for analyzing a sample of liquid (e.g., body liquid), such as, but not limited to, blood.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The technique of the present embodiments can optionally and preferably provide an effective means for analysis of body liquid from a subject. The technique of the present embodiments may be used in a wide variety of circumstances including identification and quantification of analytes that are associated with specific biological processes, physiological conditions, disorders or stages of disorders. As such, the technique of the present embodiments have a broad spectrum of utility in, for example, distinction between bacterial and viral infections, disease diagnosis, drug screening, phylogenetic classification, parental and forensic identification, disease onset and recurrence, individual response to treatment versus population bases, and monitoring of therapy.

The techniques of the present embodiments are particularly useful for measuring proteins for the diagnosis of bacterial infections, viral infections and non-bacterial, non-viral diseases. The techniques of the present embodiments can optionally and preferably employ pattern recognition algorithms for the identification of the type of infection a subject is suffering from, which in turn allows for the selection of an appropriate treatment regimen. Various embodiments of the invention address limitations of current diagnostic solutions by: (i) allowing accurate diagnostics on a broad range of pathogens; (ii) enabling rapid diagnosis (within minutes); (iii) insensitivity to the presence of non-pathogenic bacteria and viruses (thus reducing the problem of false-positive); and (iv) eliminating the need for direct sampling of the pathogen, thus enabling diagnosis of inaccessible infections. Thus, some methods of the invention allow for the selection of subjects for whom antibiotic treatment is desired and prevent unnecessary antibiotic treatment of subjects having only a viral infection or a non-infectious disease. Some methods of the invention also allow for the selection of subjects for whom anti-viral treatment is advantageous.

While some of the embodiments described herein relate to applications directed to the diagnosis of bacterial infections, viral infections and non-bacterial, non-viral diseases distinction, it is to be understood that many other applications can benefit from the technique of the present embodiments, and are therefore encompassed by at least some embodiments of the present disclosure.

FIGS. 1A-I are schematic illustrations of a top view (FIG. 1A) a side view (FIGS. 1B, 1H and 1I) and perspective views (FIGS. 1C and 1D-G) of a cartridge device 10 suitable for analyzing a liquid (e.g., body liquid), according to some embodiments of the present invention. Cartridge device 10 is particularly useful for loading to a system that is configured for automatically performing the analysis, such as, but not limited to, an automatic POC system. A representative example of a system suitable for receiving cartridge device 10 is provided below. Cartridge device 10 can be used during analysis of any type of body liquid, particularly a mammalian body liquid, e.g., a body liquid of a human.

Representative examples of body liquids contemplated according to some embodiments of the present invention include, without limitation, whole blood, a fraction of whole blood, capillary blood, serum, plasma, urine, saliva, semen, stool, sputum, cerebral spinal fluid, tears, sweat, interstitial fluid, mucus, nasal mucus, amniotic fluid, sample collected by a nasal swab, or the like. In some embodiments of the present invention cartridge device 10 is used during analysis of a whole blood of a human, in some embodiments of the present invention cartridge device 10 is used during analysis of a fraction of whole blood of a human, in some embodiments of the present invention cartridge device 10 is used during analysis of a capillary blood of a human, in some embodiments of the present invention cartridge device 10 is used during analysis of a serum of a human, and in some embodiments of the present invention cartridge device 10 is used during analysis of a plasma of a human. The cartridge device 10 also suitable for analyzing a liquid other than a body fluid, such as, but not limited to, a liquid sample from river, a liquid sample from sewage, a liquid sample from water reservoir, a liquid sample from food product, etc.

Cartridge device 10 optionally and preferably comprises a first member 12 having a plurality of wells 14 for performing assays. Wells 14 are shown arranged in a rectangular array, but other arrangements (e.g., circular array, honeycomb array, etc.) are also contemplated.

At least a portion of wells 14 contains substances for mixing with the liquid (e.g., body liquid) in order to allow performing the assays. Typically, one or more wells can contain reactive substances (e.g., antibodies) that react with one or more target substances (e.g., antigens) in the body liquid (e.g., by forming immune complexes) once contact is establish between the reactive substance in the respective well and the body liquid. One or more wells can also contain a diluent for diluting the body liquid. One or more wells can also contain a wash buffer for allowing performing assays including a wash step. As a representative example, which is not to be considered as limiting, wells 14a can contain reactive substances, wells 14b can contain a diluent, and wells 14c can contain a wash buffer, but any of wells 14 can potentially include any of the above, or other substances, as desired.

Preferably, cartridge device 10 comprises a pierceable film 22 covering wells 14 to seal wells 14 and to maintain the respective substances within wells 14, thereby preventing evaporation, flow-out, drop and/or contamination during transportation of device 10 and optionally and preferably also while loading device 10 to a receiving system, such as, but not limited to, a POC system. Pierceable film 22 can be of any type, such as, but not limited to, an aluminum laminate foil, a plastic film or the like.

The substances in wells 14 are optionally and preferably selected for use in an immunological assay utilizing an antigen-antibody reaction. Representative examples of immunological assays suitable for the present embodiments include, without limitation, an enzyme-linked immunosorbent assay (ELISA), particularly but not necessarily a sandwich ELISA, a chemiluminescent immunoassay, an immunofluorescence assay, a radioimmunoassay, immunochromatography and immunonephelometry.

For example, wells 14 can comprise one or more wells containing a first antibody immobilized on a solid carrier, optionally and preferably a solid magnetic carrier, and one or more wells containing a second antibody labeled with labeling substance, wherein the first and second antibodies are selected to specifically bind to the target substance in the body liquid. The labeling enzyme and the antibodies are optionally and preferably selected for detecting the target substance by a sandwich ELISA.

Labeling substances suitable for use according to some embodiments of the present invention include, without limitation, enzymes, free radicals, radioisotopes, fluorescent dyes, bacteriophages, or coenzymes. Representative examples of suitable enzymes including, without limitation, horseradish peroxidase and alkaline phosphatase. Representative examples of suitable fluorescent labels including, without limitation, fluorescein, Alexa, green fluorescent protein and rhodamine.

The antibodies may be monoclonal, polyclonal, chimeric, or a fragment of the foregoing, and the step of detecting the reaction product may be carried out with any suitable immunoassay.

Suitable sources for antibodies suitable for use according to some embodiments of the present invention include, without limitation, commercially available sources such as, for example, Abazyme, Abnova, AssayPro, Affinity Biologicals, AntibodyShop, Aviva bioscience, Biogenesis, Biotechne, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, Zeptometrix, Thermo Fischer scientific, Invitrogen, ATCC, Novus biologicals, Hytest, Medix, and Biospacific. However, the skilled artisan can routinely make antibodies, against any of the proteins described herein.

Polyclonal antibodies for measuring proteins include without limitation antibodies that were produced from sera by active immunization of one or more of the following: Rabbit, Goat, Sheep, Chicken, Duck, Guinea Pig, Mouse, Donkey, Camel, Rat and Horse.

Examples of additional reactive substances, include without limitation: scFv, dsFv, Fab, sVH, F(ab')$_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

In some embodiments of the present invention, the target substance in the body liquid is TRAIL. Antibodies suitable for measuring TRAIL include without limitation: Mouse, Monoclonal (55B709-3) IgG (Thermo Fisher Scientific); Mouse, Monoclonal (2E5) IgG1 (Enzo Lifesciences); Mouse, Monoclonal (2E05) IgG1; Mouse, Monoclonal (M912292) IgG1 kappa (My BioSource); Mouse, Monoclonal (IIIF6) IgG2b; Mouse, Monoclonal (2E1-1B9) IgG1 (EpiGentek); Mouse, Monoclonal (RIK-2) IgG1, kappa (BioLegend); Mouse, Monoclonal M181 IgG1 (Immunex Corporation); Mouse, Monoclonal VI10E IgG2b (Novus Biologicals); Mouse, Monoclonal MAB375 IgG1 (R&D Systems); Mouse, Monoclonal MAB687 IgG1 (R&D Systems); Mouse, Monoclonal HS501 IgG1 (Enzo Lifesciences); Mouse, Monoclonal clone 75411.11 Mouse IgG1 (Abcam); Mouse, Monoclonal T8175-50 IgG (X-Zell Biotech Co); Mouse, Monoclonal 2B2.108 IgG1; Mouse, Monoclonal B-T24 IgG1 (Cell Sciences); Mouse, Monoclonal 55B709.3 IgG1 (Thermo Fisher Scientific); Mouse, Monoclonal D3 IgG1 (Thermo Fisher Scientific); Goat, Polyclonal C19 IgG; Rabbit, Polyclonal H257 IgG (Santa Cruz Biotechnology); Mouse, Monoclonal 500-M49 IgG; Mouse, Monoclonal 05-607 IgG; Mouse, Monoclonal B-T24 IgG1 (Thermo Fisher Scientific); Rat, Monoclonal (N2B2), IgG2a, kappa (Thermo Fisher Scientific); Mouse, Monoclonal (1A7-2B7), IgG1 (Genxbio); Mouse, Monoclonal (55B709.3), IgG (Thermo Fisher Scientific); Mouse, Monoclonal B-S23*IgG1 (Cell Sciences), Human TRAIL/TNFSF10 MAb (Clone 75411), Mouse IgG1 (R&D Systems); Human TRAIL/TNFSF10 MAb (Clone 124723), Mouse IgG1 (R&D Systems) and Human TRAIL/TNFSF10 MAb (Clone 75402), Mouse IgG1 (R&D Systems).

Antibodies for measuring TRAIL include monoclonal antibodies and polyclonal antibodies for measuring TRAIL. Antibodies for measuring TRAIL include antibodies that were developed to target epitopes from the list comprising of: Mouse myeloma cell line NS0-derived recombinant human TRAIL (Thr95-Gly281 Accession #P50591), Mouse myeloma cell line, NS0-derived recombinant human TRAIL (Thr95-Gly281, with an N-terminal Met and 6-His tag Accession #P50591), E. coli-derived, (Val114-Gly281, with and without an N-terminal Met Accession #:Q6IBA9), Human plasma derived TRAIL, Human serum derived TRAIL, recombinant human TRAIL where first amino acid is between position 85-151 and the last amino acid is at position 249-281.

In some embodiments of the present invention, the target substance in the body liquid is CRP. Examples of monoclonal antibodies suitable for measuring CRP include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG, Human C-Reactive Protein/CRP Biot MAb (Cl 232024), Mouse IgG2B, Human C-Reactive Protein/CRP MAb (Clone 232007), Mouse IgG2B, Human/Mouse/Porcine C-Reactive Protein/CRP MAb (Cl 232026), Mouse IgG2A, Mouse, C-reactive protein (CRP) monoclonal antibody (clone A58014501); Mouse, C-reactive protein (CRP) monoclonal antibody (clone A58015501).

Antibodies for measuring CRP include monoclonal antibodies for measuring CRP and polyclonal antibodies for measuring CRP.

Antibodies for measuring CRP also include antibodies that were developed to target epitopes from the list comprising of: Human plasma derived CRP, Human serum derived CRP, Mouse myeloma cell line NS0-derived recombinant human C-Reactive Protein/CRP (Phe17-Pro224 Accession #P02741).

In some embodiments of the present invention, the target substance in the body liquid is IP-10. Examples of monoclonal antibodies suitable for measuring IP-10 include without limitation: IP-10/CXCL10 Mouse anti-Human Monoclonal (4D5) Antibody (LifeSpan BioSciences), IP-10/CXCL10 Mouse anti-Human Monoclonal (A00163.01) Antibody (LifeSpan BioSciences), MOUSE ANTI HUMAN IP-10 (AbD Serotec), RABBIT ANTI HUMAN IP-10 (AbD Serotec), IP-10 Human mAb 6D4 (Hycult Biotech), Mouse Anti-Human IP-10 Monoclonal Antibody Clone B-050 (Diaclone), Mouse Anti-Human IP-10 Monoclonal Antibody Clone B-055 (Diaclone), Human CXCL10/IP-10 MAb Clone 33036 (R&D Systems), Human CXCL10/IP-10/CRG-2 MAb Clone 33021 (R&D Systems), Human CXCL10/IP-10/CRG-2 MAb Clone 33033 (R&D Systems), CXCL10/INP10 Antibody 1E9 (Novus Biologicals), CXCL10/INP10 Antibody 2C1 (Novus Biologicals), CXCL10/INP10 Antibody 6D4 (Novus Biologicals), CXCL10 monoclonal antibody M01A clone 2C1 (Abnova Corporation), CXCL10 monoclonal antibody (M05), clone 1E9 (Abnova Corporation), CXCL10 monoclonal antibody, clone 1 (Abnova Corporation), IP10 antibody 6D4 (Abcam), IP10 antibody EPR7849 (Abcam), IP10 antibody EPR7850 (Abcam).

Antibodies for measuring IP-10 include monoclonal antibodies for measuring IP-10 and polyclonal antibodies for measuring IP-10.

Antibodies for measuring IP-10 also include antibodies that were developed to target epitopes from the list comprising of: Recombinant human CXCL10/IP-10, non-glycosylated proteins chain containing 77 amino acids (aa 22-98) and an N-terminal His tag Interferon gamma inducible protein 10 (125 aa long), IP-10 His Tag Human Recombinant IP-10 produced in E. Coli containing 77 amino acids fragment (22-98) and having a total molecular mass of 8.5 kDa with an amino-terminal hexahistidine tag, E. coli-derived Human IP-10 (Val22-Pro98) with an N-terminal Met, Human plasma derived IP-10, Human serum derived IP-10, recombinant human IP-10 where first amino acid is between position 1-24 and the last amino acid is at position 71-98.

Further exemplary target substances in the body liquid that can be measured in some embodiments of the present invention to assist in distinguishing between bacterial and viral infections include: IL1RA, Mac-2BP, B2M, BCA-1, CHI3L1, Eotaxin, IL1a, MCP, CD62L, VEGFR2, CHP, CMPK2, COROIC, EIF2AK2, ISG15, RPL22L1, RTN3, CD112, CD134, CD182, CD231. CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC, TNFR1, L11, CD8A, IL7, SAA, TREM-1, PCT, IL-8, IL-6, ARG1, BCA-1, BRI3BP, CCL19/MIP3b, MCP-2, ABTB1, ADIPOR1, ARHGDIB, ARPC2, ATP6V0B, C1orf83, CD15, CES1, CORO1A, CRP, CSDA, EIF4B, EPSTI1, GAS7, HERC5, IFI6, KIAA0082, IFIT1, IFIT3, IFITM1, IFITM2, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SDCBP, SMAD9, SOCS3, TRIM 22, UBE2N, XAF1 and ZBP1.

In some embodiments of the present invention the target substance in the body liquid is originated from or secreted by micro-organisms including bacteria, viruses, parasites (for example Toxoplasma gondii) or fungi. These target proteins could be any type of bacterial, viral or fungal protein including for example structural proteins, functional proteins and enzymes (for example hemagglutinin and neuraminidase of the influenza virus), secreted proteins, and microbial toxins (for example botulinum toxin produced by the bacterium Clostridium botulinum). Examples of viruses include but not limited to: Influenza A virus (Flu A), Influenza B virus (Flu B), Respiratory syncytial virus A (RSV A), Respiratory syncytial virus B (RSV B), Flu A-H1, Flu A-H1pdm09, Flu A-H3, Adenovirus (AdV), Enterovirus (HEV), Parainfluenza virus 1 (PIV 1), Parainfluenza virus 2 (PIV 2), Parainfluenza virus 3 (PIV 3), Parainfluenza virus 4 (PIV 4), Metapneumovirus (MPV), Bocavirus (HBoV), Rhinovirus (HRV), Coronavirus NL63 (CoV NL63), Coronavirus 229E (CoV 229E), Coronavirus 0C43 (CoV 0C43), Rotavirus, Smallpox, Ebola virus, Hepatitis A virus, Hepatitis C, Hepatitis B, Rubella virus, Varicella-Zoster Virus, Epstein-Barr virus, Herpes Simplex Virus, Cytomegalovirus, Measles and Mumps.

Examples of bacteria include but not limited to: Mycoplasma pneumoniae (MP), Chlamydophila pneumoniae (CP), Legionella pneumophila (LP), Haemophilus influenzae (HI), Streptococcus pneumoniae (SP), Bordetella pertussis (BP), Bordetella parapertussis (BPP), Group A streptococcus, Group B streptococcus, E coli, Bacillus anthracis, Francisella tularensis, Burkholderia pseudomallei, Treponema pallidum, Borrelia burgdorferi and Helicobacter pylori.

In some embodiments of the present invention, the measurement of micro-organism target substance is used to detect the presence of a specific pathogenic or non-pathogenic micro-organism in the body liquid. In some embodiments of the present invention, measurement of micro-organism target substance is used to quantify the levels of a specific pathogenic or non-pathogenic micro-organism in the body liquid in order to evaluate the viral or bacterial load.

The techniques of the present embodiments can also be used to measure other types of physiological markers that may help to diagnose or monitor various disease states, response to treatment, injury and biothreat exposure including for example inflammatory markers, cardiac markers, metabolic markers, endocrine markers, neurodegenerative markers, neuronal marker and cancer markers. Examples of physiological markers include: Troponin, Troponin I, TroponinT, Highly sensitive troponin, BNP, IGF-1, CK-MB, Myoglobin, CPK, AP, PTH, Galectin-3, Galectin-1, highly sensitive CRP, tin C-terminal Hydrolase-L1 (UCH-L1), Glial Fibrillary Acidic Protein (GFAP), CKB, Hemoglobin A and Hemoglobin B.

In some embodiments of the present invention, one or more of the wells contains an inhibitory solution, such as, but not limited to, a metal chelating agent, e.g., EDTA or EGTA, or an enzyme inhibitor, e.g., theophylline, vanadate or arsenate.

According to some embodiments of the present invention at least one of the wells has a tapered (e.g., conical) base. A well with a tapered base shaped has an advantage of ensuring high surface tension of the enclosed liquids, thereby preventing liquid from accumulating at the top part of the well, for example, during transportation. It was found by the inventors that it is particularly advantageous when one or more of the wells that contain the reagents (e.g., antibodies) are tapered, since the cartridge device is typically transported while the reagents are already contained within the wells.

According to some embodiments of the present invention, at least one of the wells has a non-tapered base. Such a shape has an advantage that compared to the tapered well, it has a lower risk of bubble formation when liquid is introduced into the well, for example, by pipetting during an assay. It was found by the inventors that this is particularly advantageous when the wells that are designated to contain the liquid are non-tapered, since the assay is typically performed by adding a sample of the liquid (e.g., body liquid) to the well.

Thus, the present embodiments contemplate a cartridge device that comprises a first plurality of wells, each having a tapered base; and a second plurality of wells. The two pluralities of wells are formed in a monolithic structure. At least some of the wells of the first plurality of wells contain a reagent therein. In some embodiments of the present invention one or more of the wells of the first plurality of wells is empty. One or more of the wells of the second plurality of wells is empty. In use, one or more of the empty wells of the second plurality of wells is optionally and preferably filed with a liquid to be analyzed, such as, but not limited to, a body liquid. Optionally, one or more of the wells of the second plurality of wells contain a reagent therein.

Referring again to FIGS. 1A-I, cartridge device 10 optionally and preferably comprises a waste collecting chamber 24 (see, FIG. 1D). Waste collecting chamber 24 can optionally and preferably, but not necessarily, comprise a moisture absorber (not shown), such as, but not limited to, a hygroscopic material, a sponge, cellulose fibers, a charcoal, an activated charcoal, a molecular sieve, and/or one or more moisture absorbing substances including, without limitation, a salt, lithium chloride, calcium chloride, magnesium chloride, phosphorus pentaoxide, silica gel, zeolite, sodium sulfate, activated alumina and activated carbon. Use of hygroscopic material is particularly advantageous since it assists in reducing probability of biohazard. A contaminated fluid is less likely to escape from the waste chamber because it is entrapped within the hygroscopic material. In some embodiments of the present invention, waste collecting chamber 24 extends to beneath, but is physically separated from, wells 14.

The waste collecting chamber is optionally and preferably covered by a structure (not shown) such as, but not limited to, a pierceable foil, a non-flexible openable lid, a flexible openable lid, and a one way valve. For example, the structure covering the waste collecting chamber can be a foil, which is pierced to expose a waste collecting chamber before deposing waste to it. The sealing foil is optionally capable of being pierced several times in the same location.

The covering structure can optionally and preferably be in a form of a labyrinth, so that the waste can only escape the cartridge if the device is rotated and inverted in a very specific manner. This significantly reduces the probability for the liquid to inadvertently escape the cartridge. Such a covering structure can be used to cover only the waste collecting chamber 24, or only the wells 24, or both the waste collecting chamber 24 and the wells 14.

Figure 1B:
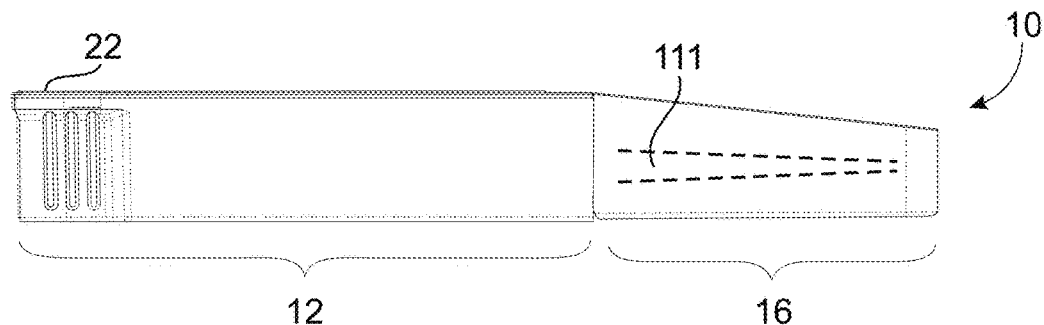
Figure 1C:
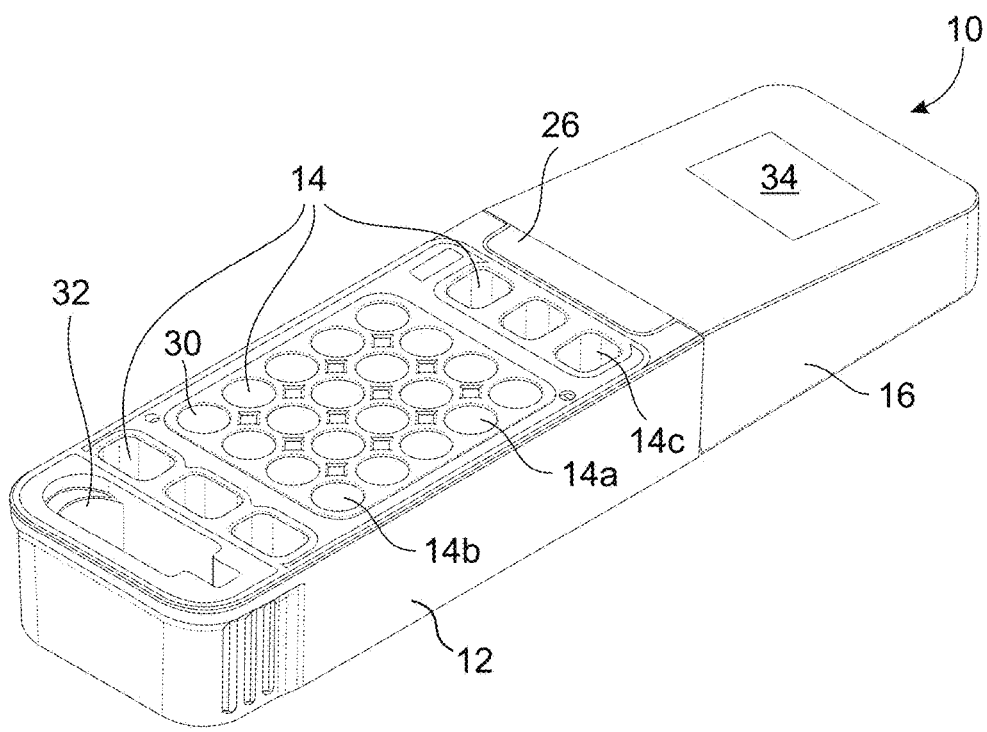
Figure 1D:
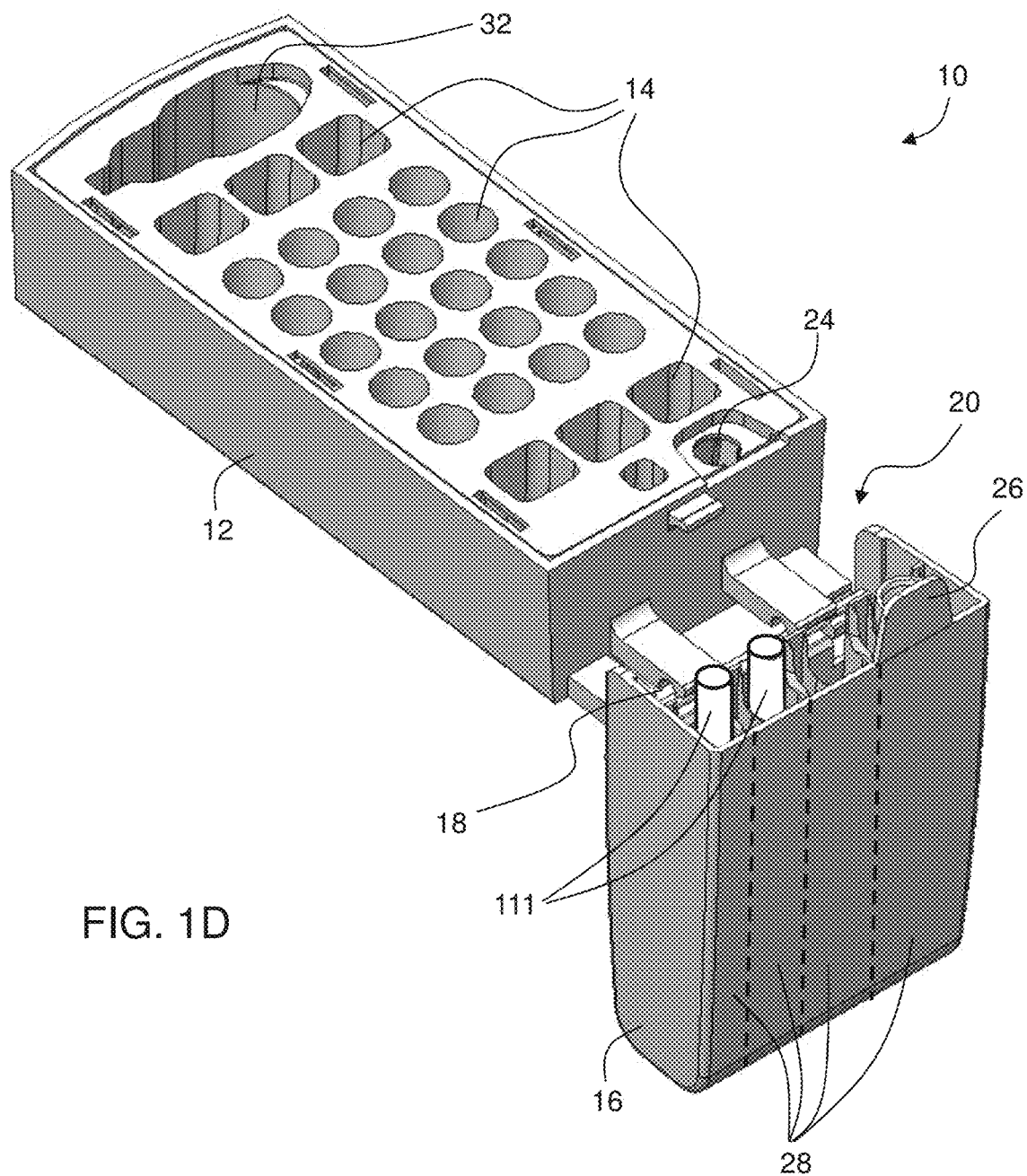

While FIG. 1D illustrates waste collecting chamber 24 as a having single chamber, this need not necessarily be the case, since, the present embodiments also contemplate waste collecting chamber haven multiple separated chambers or sub-chamber, that may be connected thereamongst of separated from each other, for example, by sponge or hygroscopic partition that absorbs waste. These embodiments are particularly useful when it is desired not to access the same preventing the same waste collecting chamber more than once, in which caser each chamber is a single use chamber, into which there is a single deposing of waste. Alternatively, or additionally, the waste collecting chamber can comprise several entrance points.

Figure 12:
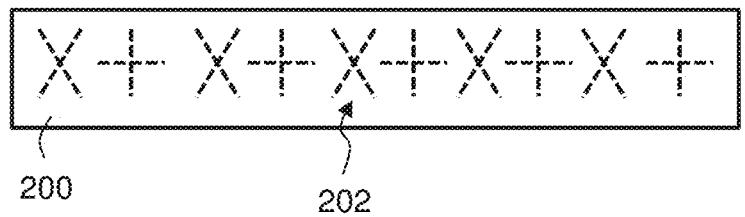
FIG. 12 is a schematic illustration of a covering label scored with a plurality of patterns to form frangible piercing locations, according to some embodiments of the present invention.

The waste collecting chamber sealing foil or the wells sealing foil can be covered by a label 200, as illustrated in FIG. 12. Optionally and preferably, the covering label 200 is scored or partially cut along a pattern 202 to form a frangible piercing location defined by pattern 202. Optionally and preferably, there is a plurality of frangible piercing locations, each defined by a respective scored pattern, as illustrated in FIG. 12. Two or more adjacent scored patterns (e.g., each pair of adjacent scored patterns) can be separated from each other. The scored pattern has a shape of, for example, a cross or a star. The cross can be a right angle cross, e.g., shape of a plus symbol, or an acute angle cross, e.g., shape of an X symbol. In some embodiments of the present invention, two or more adjacent scored patterns (e.g., each pair of adjacent scored patterns) have shapes of differently oriented crosses or differently shaped crosses, to ensure that the scored patterns are separated from each other. Separating between the scored patterns is advantage from the standpoint of preventing cross-talk between different entry locations to the chamber or different wells.

According to some embodiments of the invention, the scored patterns comprise right angle crosses, e.g., shape of plus symbols, and acute angle crosses, e.g., shape of X symbols, arranged in alternating manner.

Cartridge device 10 optionally and preferably comprises a second member 16. In some embodiments of the present invention second member 16, is connected to first member 12. In preferred embodiments of the invention second member 16 is connected to first member 12 by a hinge 18 (FIG. 1D) allowing a rotation of one of the two members 12 and 16 with respect to the other about hinge 18. Preferably, hinge 18 is configured to allow rotation to form an angle of at least 70° or at least 80° or at least 90° between members 12 and 16.

Figure 1E:
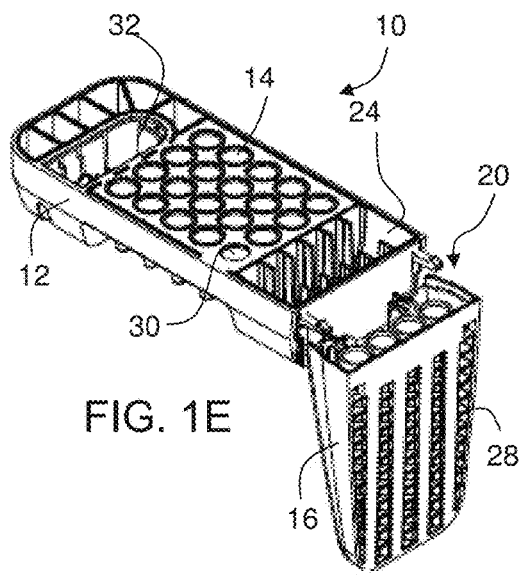
Figure 1F:
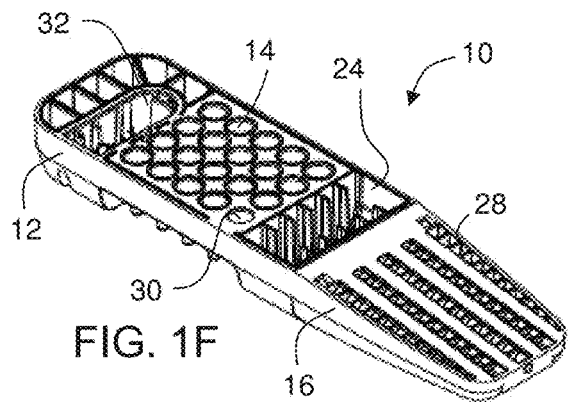
Figure 1G:
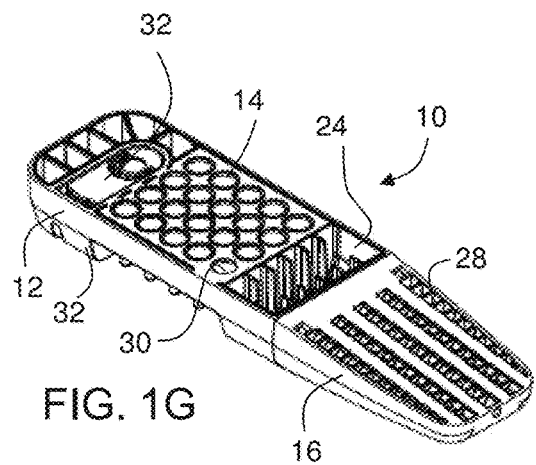
Figure 1H:
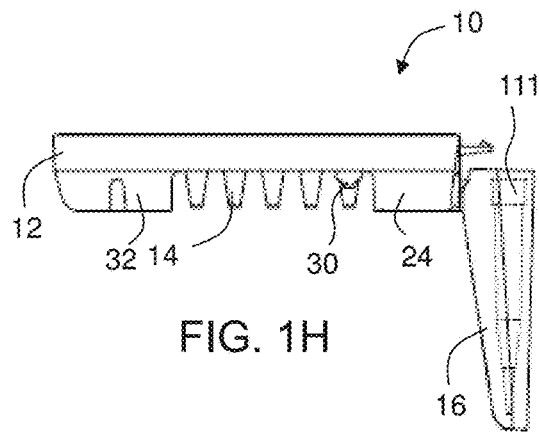
Figure 1I:
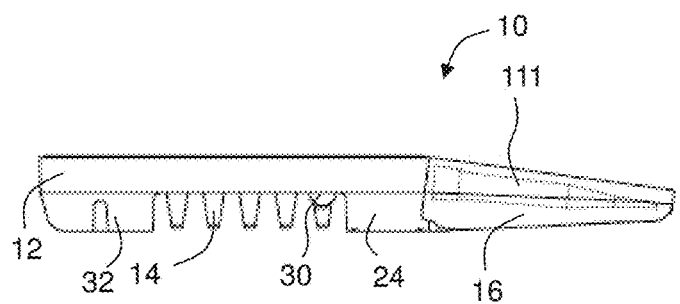
Figure 4:
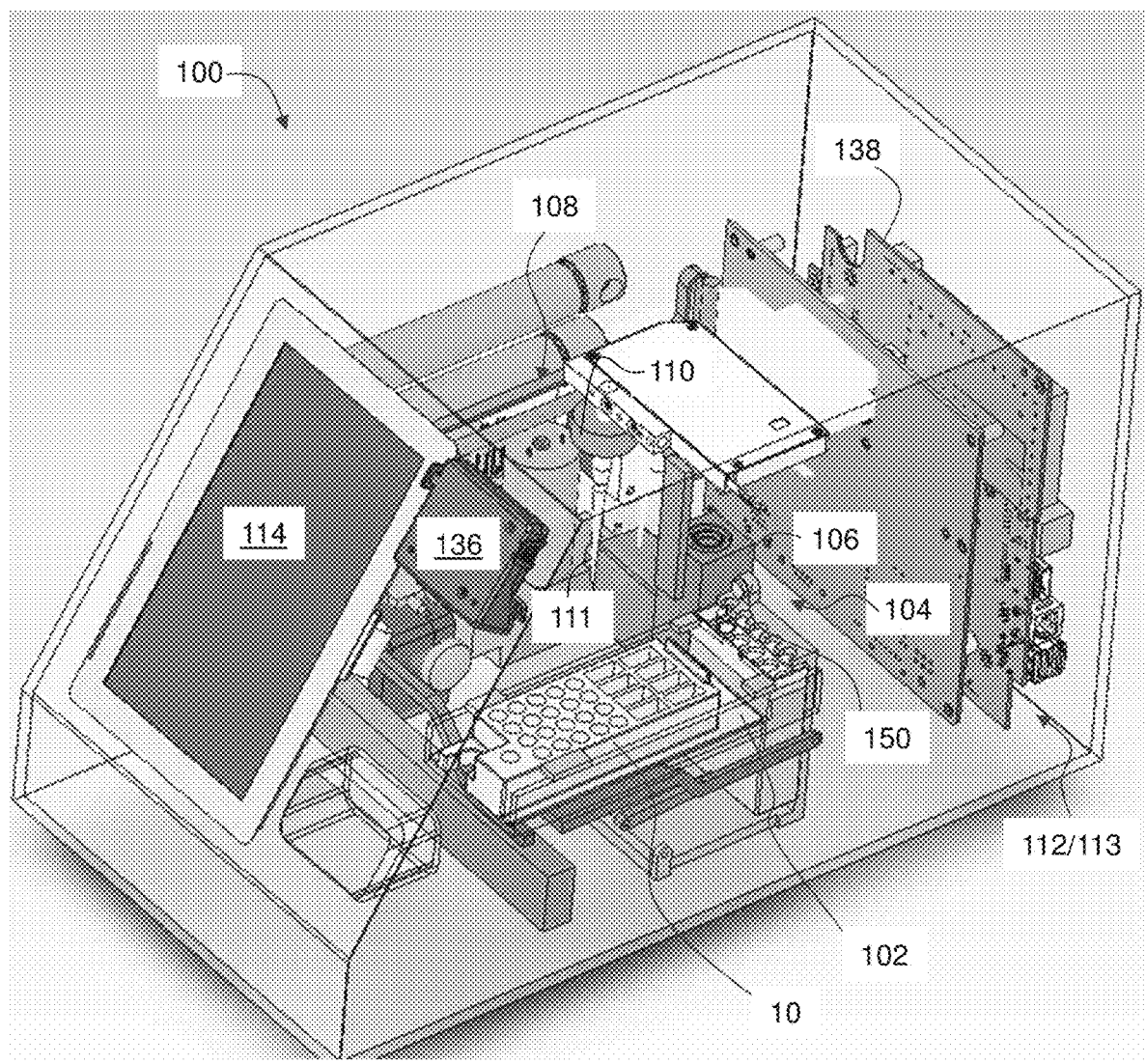
FIG. 4 is a schematic illustration of a system for analyzing a liquid (e.g., body liquid), according to some embodiments of the present invention.

The second member 16 can in some embodiments of the present invention be slideably connected to first member 12, as schematically illustrated in FIGS. 13A and 13B. In these embodiments, device 10 can be distributed to the users in a state in which second member 16 covers or partially covers first member 12. In use, second member 16 can slide over first member 12 to expose the wells (or the structure, such as, but not limited to, the sealing foil or label that covers the wells, when employed). Following this sliding, the second member 16 can be completely detached from first member 12, or can remain hinged to first member 12 in a similar manner that is illustrated in FIGS. 1D-F. In embodiments in which second member 16 slides over first member 12, the length of device 10 is shorter than in embodiments in which the members 12 and 16 are connected by hinge 18.

The second cartridge member can in some embodiments of the present invention be separated from the first cartridge member in a manner that they are not to be connected. These embodiments are useful when it is desired to load the two cartridge members separately to a system that is configured for automatically performing the analysis, such as, but not limited to, an automatic POC system.

Second member 16 optionally and preferably comprises a compartment 20 (shown in FIGS. 1D and 1E) for holding at least one disposable pipette tip 111 (shown in FIGS. 1A, 1B and 1D). Optionally, as illustrated in FIG. 1D, when first member 12 is held horizontally, and second member 16 is rotated downwards about hinge 18, the compartment 20 holds the pipette tips in a generally upright orientation (e.g., with a deviation of ±20° relative to the direction of gravity). In various exemplary embodiments of the one or more disposable pipette tips 111 are already within compartment 20, preferably in sterile condition, before the aforementioned rotation of one of the members 12 and 16 (see FIGS. 1A and 1B)

In some embodiments of the present invention waste collecting chamber 24 is covered by a lid 26 connected to or being an extension of second member 16. In these embodiments, when second member 16 is hinged to a generally upright orientation, lid 26 is hinged together with second member 16 and collecting chamber 24 is exposed, as illustrated in FIG. 1D.

The present embodiments also contemplate configurations in which the waste collecting chamber 24 is part of the second member 16. Representative examples of these embodiments are illustrated in FIGS. 16A-D. Also contemplated, are embodiments in which there is a first waste collecting chamber 24, which is part of first member 12, and a second waste collecting chamber, which is part of the second member 16.

Cartridge device 10 can optionally and preferably comprise one or more identifiers 34 disposed on one of its external walls. In the illustrations of FIGS. 1A and 1C, which are not to be considered as limiting, identifier 34 is on the upper wall of member 16, but any other wall can be used to carry identifier 34. Further, more than one identifier can be used, on a respective more than one wall. Identifier 34 can be embossed, debossed or printed, and can be of any type such as, but not limited to, a set of machine-readable symbols, e.g., one-dimensional or barcode symbols, two-dimensional or matrix or area code symbols, or combinations thereof. Also contemplated are other types of identifiers, including, without limitation, a magnetic recording device, an electronic chip, such as, but not limited to, an RFID chip, or the like.

Identifier 34 can optionally and preferably encode information pertaining to the contents of wells 14 and/or to the identity of the subject whose body liquid is to be analyzed. Identifier 34 can, in some embodiments of the present invention, encode other types of information, such as, but not limited to, information on the type of target substance to be analyzed, reagent management information, and information on a calibration curve for use in the analysis. When an automatic system, e.g., a POC system, is provided with a device that reads the information from identifier 34, the operator of the system can merely load cartridge device 10 to such a system without the need to manually operate a work sheet, which is a major cause of an error in conventional POC settings. In some embodiments of the present invention, the record of the information on identifier 34 is configured to be destroyed once cartridge device 10 is used, so as to allow determining whether a particular cartridge device item has been used or is unused. This, can be done, for example, by providing identifier 34 on a seal of film, such as, but not limited to, film 22, that needs to be pierced or broken before performing the assay.

In some embodiments of the present invention compartment 20 of second member 16 is partitioned into a plurality of partitions 28, each constituted for holding one pipette tip. The partitions can be isolated from each other (namely devoid of fluid communication thereamongst). Alternatively, partitions can be partial in which case partitions 28 are not isolated from each other, and allow some fluid communication thereamongst.

Partitions 28 can be arranged in any geometrical arrangement within compartment 20. Non-limiting examples for arrangements of partitions 28 in member 16 are illustrated in FIGS. 2A-I. FIGS. 2A, 2D and 2G illustrate the internal arrangement of partitions 28 in compartment 20, FIGS. 2B, 2E and 2H respectively show cartridge device when member 16 is not hinged, and FIGS. 2C, 2F and 2I respectively show a perspective view of member 16 once hinged to a vertical orientation. In FIGS. 2A-C, the cross sections of partitions 28 are arranged along the sides of a trapezoid, in FIGS. 2D-F, the cross sections of partitions 28 are arranged along the sides of a square, and in FIGS. 2G-I, the cross sections of partitions 28 are arranged along a straight. Arrangements to form other geometrical shapes are also contemplated. Although FIGS. 2A-I all show four partitions in compartment 20, this need not necessarily be the case, since, for some applications, more or less than four partitions can be employed. Preferably, the number of partitions equals at least the number of assays for which device 10 is to be used.

Aside for holding the substances in wells 14 and the disposable tips 111 in compartment 20, device 10 is preferably also configured for holding the liquid (e.g., body liquid). This can be done in more than one way.

In some embodiments of the present invention device 10 comprises a sample chamber 30 for holding the liquid (e.g., body liquid). Chamber 30 can be enacted by one of well 14 or it can be an additional chamber of device 10, as desired. In embodiments in which cartridge device 10 comprises pierceable film 22, film 22 preferably covers all wells 14 except chamber 30, as illustrated in FIGS. 2B, 2E and 2H.

In some embodiments of the present invention, the liquid (e.g., body liquid) is provided in a separate container. In these embodiments, first member 12 of device 10 optionally and preferably comprises a cavity 32 constituted for receiving and fittedly holding a container 40 (not shown in FIGS. 1A-D, see FIGS. 3A-K) containing the liquid (e.g., body liquid).

Any of the above configurations for introducing the liquid (e.g., body liquid) into device 10 can be used for any type of liquid (e.g., body liquid). A preferred, albeit not exclusive, use of container 40 is when the body liquid is a whole blood or capillary blood sample, and a preferred, albeit not exclusive, use of chamber 30 is for other types of body liquids, e.g., a serum, a nasal mucus sample, etc. The procedure for loading the body liquid into device 10 may optionally, but not necessarily, also be selected based on the clinical setting in which the operation. For example, use of container 40 is advantageous at a POC clinic, and use of chamber 30 is advantageous at facilities with a central laboratory (e.g., hospitals or research facilities).

Cartridge device 10 can, in some embodiments of the present invention, include both chamber 30 and cavity 32. In these embodiments, when cartridge device 10 is intended for analysis of a liquid (e.g. body liquid) contained in chamber 30 (e.g., for analysis of serum collected in a hospital), cavity 32 is optionally sealed and is not in use, and when cartridge device 10 is intended for analysis of a liquid (e.g., body liquid) contained in container 40 (e.g., analysis of capillary blood collected at a POC facility), chamber 30 is optionally sealed and is not in use. In some embodiments of the present invention cartridge device 10 is accompanied by instructions for use. For example, when cavity 32 is sealed the instructions can include an indication that the liquid (e.g., body liquid) is to be introduced into chamber 30 and that cavity 32 is not to be used, and when chamber 30 is sealed the instructions can include an indication that the liquid (e.g., body liquid) is to be introduced into a separate container (e.g., container 40 described below) which is to be loaded into cavity 32 of device 10, and that chamber 30 is not to be used.

Also contemplated, are embodiments in which the operator is allowed to use both container 40 and chamber 30. In these embodiments, container 40 and chamber 30 optionally and preferably contain different types of liquids (e.g., different types body liquids). Any combination of different types of liquids, such as, but not limited to, the types of body liquids listed above, is contemplated. Loading two different types of body liquids into the same cartridge device is useful, when it is desired to detect the presence or measure the level of more than one target substance, wherein at least two target substances potentially reside in different types of body liquids. For example, one type of body liquid can be used for detecting the presence or measuring the level of a target substance indicative of the subject's response to a potential infection, and another type of body liquid can be used for detecting the presence or measuring the level of a target substance indicative of presence or level of a disease causing agent, such as, but not limited to, a micro-organism (e.g., a bacterium, a virus or a fungus). As a representative example, which is not to be considered as limiting, container 40 can contain a capillary blood sample, and chamber 30 can contain a nasal mucus sample. The capillary blood sample in container 40 can be analyzed to detect, e.g., host proteins, and the nasal mucus sample can be analyzed to detect, e.g., micro-organism related proteins.

Figure 14A:
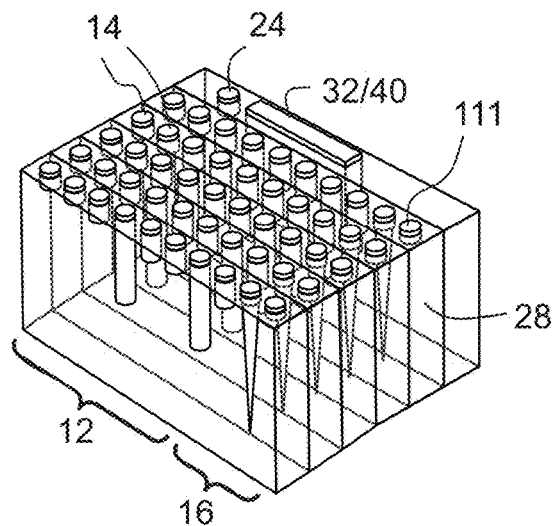
FIGS. 14A and 14B are schematic illustrations of a cartridge device in which wells are arranged in rows, wherein in each row the wells and the tips are co-linear with each other, according to some embodiments of the present invention.
Figure 14B:
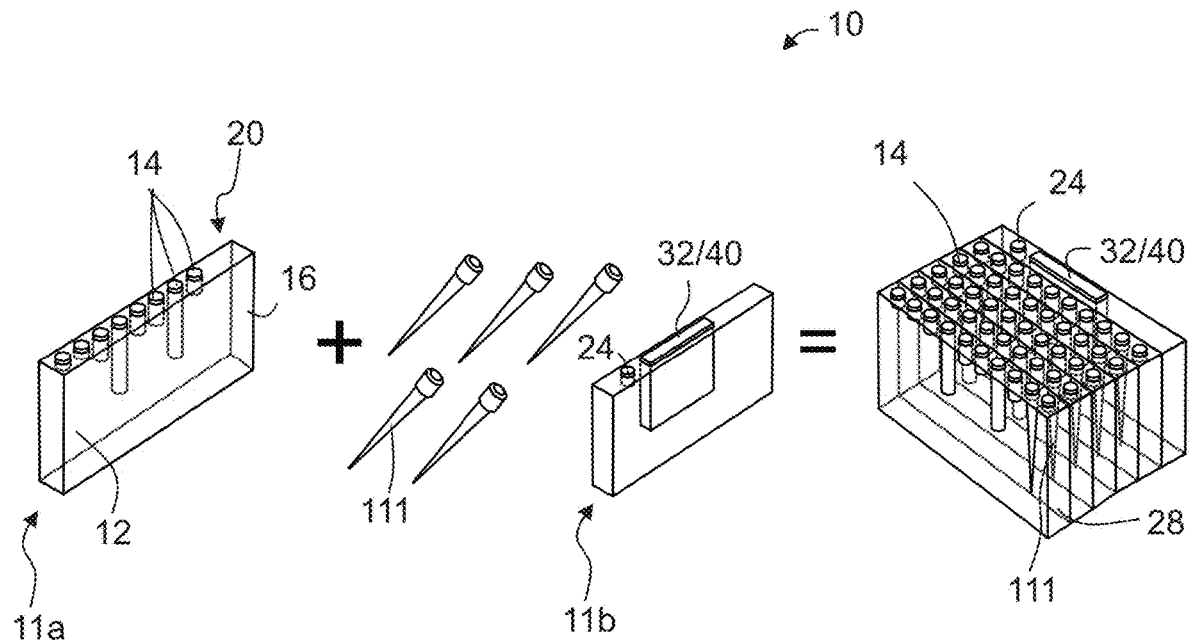
Figure 16A:
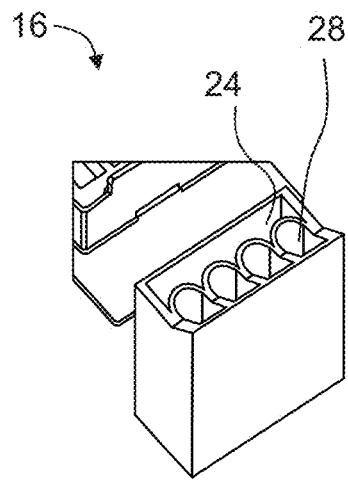
FIGS. 16A-D are schematic illustrations of a member of a cartridge device that contains compartments for pipette tips and a waste collecting chamber, according to some embodiments of the present invention.
Figure 16B:
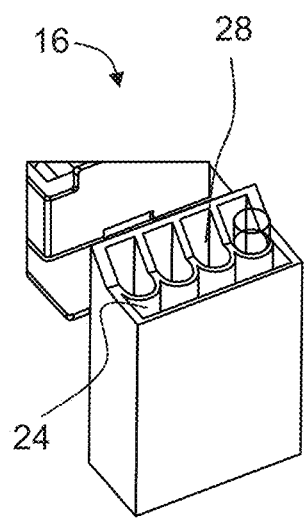
Figure 16C:
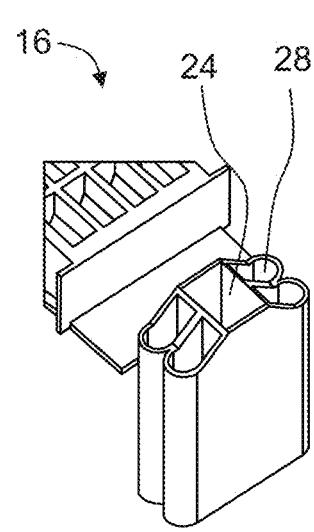
Figure 16D:
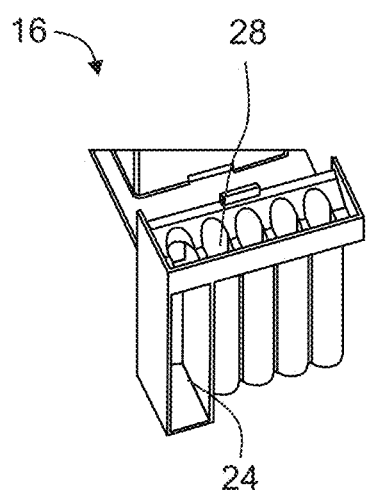

The present embodiments also contemplate configurations in which the two members 12 and 16 are co-linear with each other. Such a configuration is illustrated in FIGS. 14A and 14B. Shown is a configuration in which wells are arranged in rows, wherein in each row the wells 14 and the partition 28 are co-linear with each other. Each row provides the substances and tip that are to be used in a single assay. Specifically, the wells 14 at a particular row contain the substances that are to be used for the assay, and the partition 28 at that particular row contains the tip 111 in which the assay is to be executed as described below. The cavity 32 for receiving container 40 and the waste collecting chamber 24 can be arranged on a separate row.

Device 10 can have several connectable modular elements, each optionally having a respective portion of the first and second members, and constituted for performing a different assay. For example, when the wells 14 and the partition 28 are co-linear with each other and are arranged in rows, the rows can enact the modular elements. This embodiment is illustrated in FIG. 14B showing a modular element 11a in the form of a single row having member 12 with a plurality of wells 14, and member 16 with a compartment 20 for holding a tip. Several such modular elements 11a can be assembled together and the tips 111 can be introduced into the compartment 20 of each modular element 11a. The modular elements 11a can be further assembled with an additional modular element 11b that includes cavity 32 for receiving container 40 and the waste collecting chamber 24, to form the cartridge device illustrated at the right panel of FIG. 14B. The modular approach is advantageous since it allows flexibility with manufacturing line and product pipeline. For example: one modular element 11a can be fabricated to detect one set of protein (e.g., CRP, IP10 and TRAIL), and another modular element 11a can be fabricated to detect another set of proteins (e.g., CRP, PCT, ILFLUENZA-related protein and MX1).

Device 10 can have any shape. Preferably, the shape is compatible with a cartridge holder of a system that receives device 10 and performs the analysis (see FIGS. 11A-C). FIGS. 1A through 21, and 14A and 14B illustrate embodiments in which device 10 has a shape defined by a generally polygonal cross-section along the horizontal plane. For example, device 10 can have a shape of a cuboid, preferably with round edges, or several cuboids preferably with round edges, (e.g., each of members 12 and 16 is shaped as a cuboid with round edges). However, this need not necessarily be the case, since some embodiments of the present invention contemplate a cartridge device with a shape defined by a round cross-section along the horizontal plane. These embodiments are illustrated in FIGS. 15A and 15B. In the embodiment illustrated in FIG. 15A device 10 has a shape of cylinder, but embodiments in which device 10 has shape of a cylindrical sector or other round shapes are also contemplated.

In embodiments in which device 10 has a shape defined by a round cross-section along the horizontal plane (e.g., as illustrated in FIG. 15A), it can also be assembled from a plurality of modular elements. For example, each modular elements can have a shape of a cylindrical sector, as illustrated in FIG. 15B. In the embodiment illustrated in FIG. 15A, member 12 is assembled from several modular elements 11a, each containing a plurality of wells 14 and compartment 20 for holding the tips (not shown), but other arrangements are also contemplated according to some embodiments of the present invention.

FIGS. 3A-K are schematic illustrations of a container 40 suitable for being loaded into cavity 32 of device 10, according to some embodiments of the present invention.

In some embodiments of the present invention container 40 has a flat base 46. The advantage of these embodiments is that the flat base 46 ensures that container 40 can be stably place on a surface, such as a desk. Another advantage is that the flat base provides more area to attach labels and stickers, such as, but not limited to, identification label. Container 40 optionally and preferably has an internal compartment 42 for holding the liquid (e.g., body liquid). Compartment 42 is typically from about 5 µl to about 500 µl or from about 50 µl to about 350 µl or from about 100 µl to about 300 µl in volume. Such a volume is sufficiently small to be considered non-threatening psychologically, particularly when the subject is a child, but still succulently large to allow accurate measurement of multiple target substances. An inner wall of compartment 42 is optionally and preferably coated, at least partially, with an anticoagulant.

Preferably, compartment 42 is transparent to visible light to provide the practitioner with a view of the liquid (e.g., body liquid). Height reference marks 44 can optionally and preferably be provided on the wall of compartment 42 to indicate the recommended maximum and minimum filling heights of the liquid (e.g., body liquid) within compartment 42.

Container 40 preferably comprises a lid 48 that seals the internal compartment 42 to preventing coagulation, evaporation, flow-out, drop and/or contamination during transportation of container 40 and optionally and preferably also while loading of container 40 into cavity 32 of device 10. The lid 48 optionally and preferably prevent the anticoagulant from being exposed to oxygen, hence to preserves its efficacy in preventing coagulation. The lid 48 is also useful since it allows carrying container 40 into from one place to another with reduced or no biohazard exposure. The lid 48 is also useful for allowing to collect several samples in a remote location (e.g, pediatric ward, retirement home).

Lid 48 can be foldable or hingedly connected to the body of container 40. In some embodiments of the present invention lid 48 is pierceable, to allow extracting samples of the liquid (e.g., body liquid) from compartment 42 for analysis. This can be achieved, for example, by making the portion of lid 48 that is above compartment 42 in the form of a pierceable film 50. Film 50 the can be of any type, such as, but not limited to, an aluminum laminate foil, a plastic film or the like.

In some embodiments of the present invention container 40 is provided with gripping ribs 52 allowing the operator to hold the container 40 in a comfortable manner.

Figure 17A:
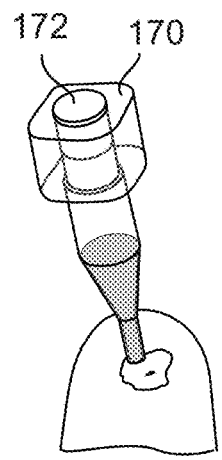
FIGS. 17A-F are schematically illustrations of a container for holding liquid (e.g., body liquid), according to some embodiments of the present invention.
Figure 17B:
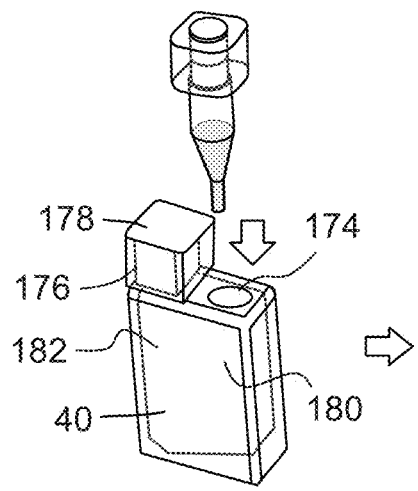

FIGS. 17A-F are schematically illustrations of container 40 in other embodiments of the present invention. In these embodiments, liquid (blood in the present illustration) is drawn out of the body by a capillary collector 170 having a sealing element 172 (e.g., a sealing rubber) thereon (FIG. 17A). Container 40 can have two cavities: a first cavity 180 receives the capillary collector 170, and a second cavity 182 is in fluid communication with the first cavity 180 and is constituted to receive from the first cavity 180 liquid 186 drawn out of the capillary collector 170.

Figure 17C:
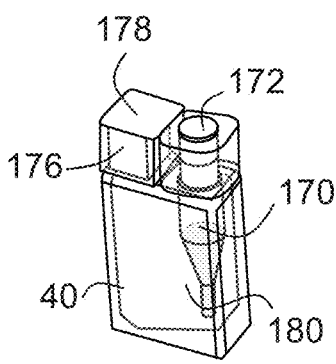
Figure 17D:
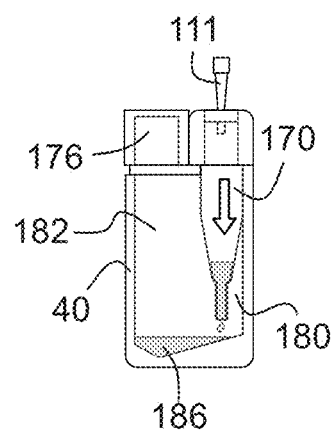
Figure 17E:
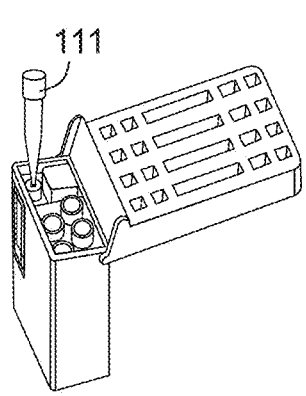
Figure 17F:
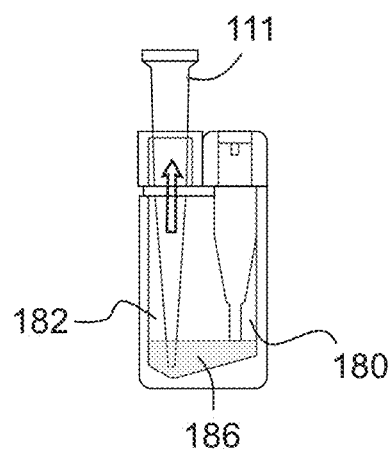
Figure 18A:
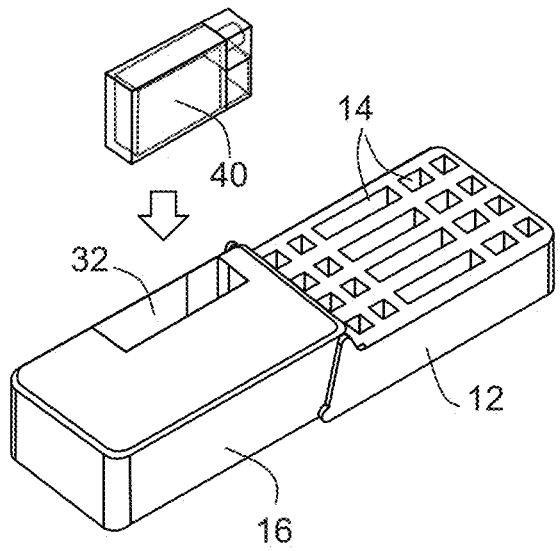
FIGS. 18A-C are schematically illustrations of a cartridge device suitable for receiving the container of FIGS. 17A-F, according to some embodiments of the present invention.
Figure 18B:
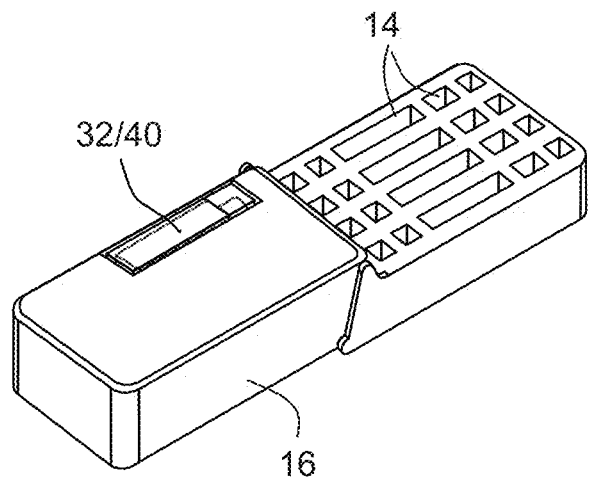
Figure 18C:
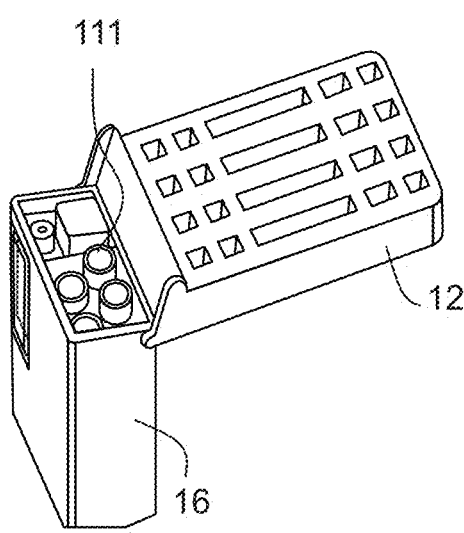

Once the liquid is in capillary collector 170, capillary collector is introduced (FIG. 17B) into an opening 174 of container 40, such that sealing element 172 engages the container's body and seals opening 174 (FIG. 17C). Container 40 optionally and preferably has another opening 176 that is covered by a sealing foil 178. In use, tip 111 is pulled from member 16 of device 10 (FIG. 17E), and is brought into contact with element 172 to pierce element 172 (FIG. 17D). Air or diluent is forced out of tip 111 so as to extract the liquid (e.g., body liquid) out of capillary collector 170, and into the cavity of container 40 (FIG. 17D). Thereafter, tip 111 is brought into contact with foil 178 to pierce foil 178 and to aspirate the body fluid from container 40 (FIG. 17F). A representative example of a configuration of device 10 suitable for these embodiments is illustrated in FIGS. 18A-C. In these embodiments cavity 32 for receiving container 40 is formed in second member 16, and container 40 is introduced into cavity in horizontal orientation. Once member 16 is hinged, container 40 assumes a generally upright orientation and the procedure described in FIGS. 17D-F is executed.

Device 10 and container 40 can be provided as a kit for analyzing the liquid (e.g., body liquid). The kit can include device 10 and container 40 in the same packaging or more preferably in separate packaging.

In use of the kit, the lid 48 of container 40 is opened and the liquid (e.g., body liquid) is transferred, preferably directly from the subject, into compartment 42. For example, when the body liquid is blood, a blood vessel in a finger of the subject can be pierced and the finger of subject can be guided to cover compartment 42 such that the blood exits the blood vessel and enters compartment 42. The lid 48 is then closed to seal compartment 42, and container 40 is placed in cavity 32 of device 10. Preferably, an acoustical indication (e.g., a click) or mechanical detent is effected when container 40 is fittedly placed in its position, for example, by means of a snap-in mechanism (not shown) mounted on container 40 and/or in cavity 32. Thus, container 40 collects the liquid directly from the subject, and is then placed as is in cartridge device 10. This is advantageous over conventional blood collecting devices which require a two-step operation in which first the blood is collected, e.g., by a capillary device, and then transferred from the capillary device to a container.

The advantage of having container 40 as a separate element from cartridge device 10, is that it allows using of the same cartridge for different sample types, thereby eliminating manufacturing issues. For example, the same type of cartridge device 10 can be used with serum, blood, saliva, and the like. Another advantage is that the cartridge without the liquid sample can be stored in a refrigerator, allowing using container 40 for sampling the liquid away from the cartridge.

Cartridge device 10 and/or container 40 can be made of any material known in the art of disposable devices. In some embodiments, at least one of the components of cartridge device 10 and/or container 40 is constructed of a polymeric material. Non-limiting examples of materials suitable for the present embodiments include polystyrene, polycarbonate, polypropylene, polydimethysiloxanes (PDMS), polyurethane, polyvinylchloride (PVC), polysulfone, polymethylmethacrylate (PMMA), acrylonitrile-butadiene-styrene (ABS), and glass.

Cartridge device 10 and/or container 40 or one or more of the subcomponents thereof can be manufactured by variety of methods including, without limitation, stamping, injection molding, embossing, casting, blow molding, machining, welding, ultrasonic welding, thermal bonding and three-dimensional printing. The subcomponents of cartridge device 10 and/or container 40 can be affixed to each other by any known technique, including, without limitation, thermal bonding, ultrasonic welding, friction fitting (press fitting), adhesives or, a natural adhesion between the two components FIGS. 4-7 are schematic illustrations of a system 100 for analyzing a liquid (e.g., body liquid), according to some embodiments of the present invention. System 100 can be used as a POC system. System 100 comprises a cartridge holder 102, adapted for receiving a cartridge device, such as, but not limited to, cartridge device 10, and an internal analyzer system 104, having an analysis chamber 106 and being configured for analyzing the liquid (e.g., body liquid) when enclosed in analysis chamber 106. In embodiments in which members 12 and 16 are separated from each other, system 100 preferably comprises two cartridge holders 102 such that each of members 12 and 16 is loaded separately into system 100. While, for clarity of presentation FIGS. 4-7 show only one cartridge holder, one of ordinary skills in the art, provided with the details described herein would know how to adjust system 100 to the case in which each of members 12 and 16 is loaded into a separate cartridge holder.

System 100 can also comprise a robotic arm system 108 carrying a pipette 110 having a disposable tip 111. Pipette 110 can be a controllable air displacement pipette, as known in the art, and tip 111 can be detachable from pipette 110. System 100 further comprises a controller 112 configured for controlling robotic arm system 108 to establish a relative motion between device 10 and pipette 110 such that tip 111 of pipette 110 sequentially visits at least cartridge device 10 and analysis chamber 106. Controller 112 optionally and preferably ensures that pipette 110 connects to, and picks up, one of the tips 111 in compartment 20 of device 10 (see FIG. 1D) before visiting wells 14 and container 40 or chamber 30, and further ensures that pipette 110 releases tip 111 into compartment 20, after visiting analysis chamber 106. Controller 112 optionally also configured to control pipette 110 (e.g., by controlling piston motions within pipette 110) to aspirate liquids into tip 111 and/or dispense liquid out of tip 111. Controller 112 optionally and preferably receives signals from a data processor 113. Preferably, but not necessarily, both controller 112 and data processor 113 are mounted on the same control board 138.

System 100 optionally and preferably comprises a display 114 for displaying information thereon. For example, display 114 can receive display instructions from internal analyzer system 104 to display the results of the analysis performed by internal analyzer system 104. In some embodiments of the present invention, system 100 comprises a reader device 136 for reading information stored on device 10, for example, by means of identifier 34 (not shown, see, e.g., FIG. 1A). Reader device 136 is compatible with the type of storage on device 10. For example, when device 10 comprises an identifier in the form of a barcode, reader device 136 can be embodied as an optical barcode reader device, and when device 10 comprises an identifier in the form of an electronic chip, e.g., an RFID chip, reader device 136 can be embodied as an RFID reader device.

In some embodiments of the present invention, system 100 employs an analysis protocol based on the information read by reader device 136, for example, by selecting a protocol from a list of protocols recorded on a computer readable medium accessible by data processor 113. Alternatively, the list of protocols can be recorded on an external computer readable medium, in which case the information read by reader device 136 is optionally and preferably transferred over a network to an external computer (not shown), that selects the protocol from the list of protocols and transfers it to system 100. The protocol to be run by system 100 may comprise instructions to controller 112 to perform the protocol, including but not limited to a particular assay to be run and a detection method to be performed.

In some embodiments of the present invention, system 100 comprises a magnet 150, for applying a magnetic field.

The magnet 150 can be a permanent magnet or an electromagnet, as desired. Magnet 150 is particularly useful when wells 14 of device 10 comprise one or more wells containing an antibody that is immobilized on a solid magnetic carrier. The magnetic field generated by magnet 150 can then be used for separating the target substance from other components in tip 111 of pipette 110, as further detailed hereinabove.

In some embodiments of the invention, there is more than one magnet which performs part or all the task of separating the target substance from other components in tip 111.

Figure 5A:
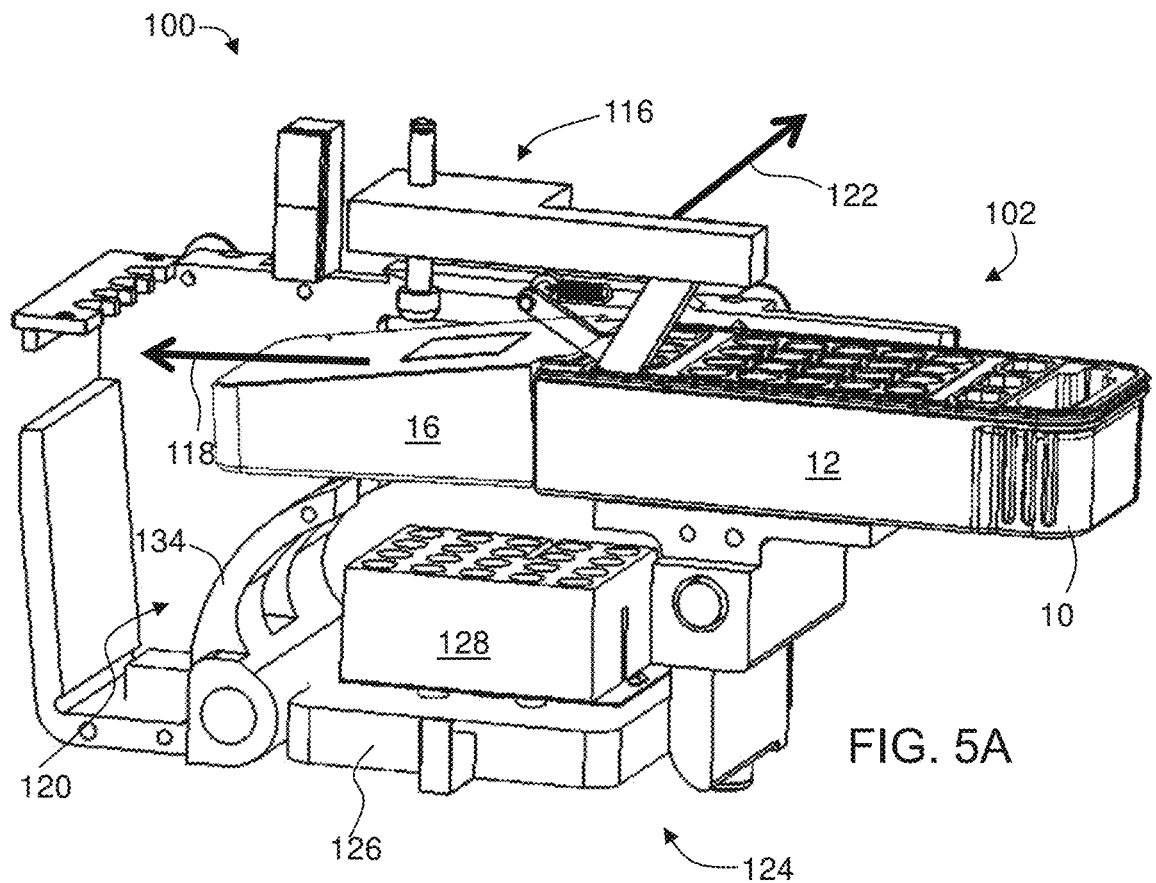
FIGS. 5A-D are schematic illustrations showing partial laid-open views of the system shown in FIG. 4, according to some embodiments of the present invention.

A partial laid-open view of system 100, illustrating cartridge holder 102 according to some embodiments of the present invention is provided in FIG. 5A. As shown, in these embodiments cartridge holder 102 comprises a lever system 116 for automatically hinging the second member 16 of device 10, when cartridge holder 102 receives device 10. In embodiments in which the first and second members of device 10 are slideably connected, lever system 116 is configured for automatically sliding the second member over the first member and hinging the second member. Lever system 116 is preferably controlled by controller 112, automatically upon receipt of device 10 by holder 102. In some embodiments of the present invention, controller 112 controls lever system 116 to draw device 10 inwardly along directing 118 prior to the hinging of second member 16. A recess 120 is optionally and preferably also provided for fixing second member 16 in its vertical position after member 16 is hinged by level system 116. Once cartridge device 10 is in its position, controller 112 preferably controls lever system 116 to disengage from device 10, for example, upward and forward along direction 122.

In some embodiments of the present invention, system 100 comprises a heating system 124. Heating system 124 can be of any type. The heating system can be configured to heat the cartridge by conduction, radiation and/or convection. In some embodiments of the present invention, the heating system heats the cartridge device by conduction. Alternatively, the heating system heats the cartridge device by radiation or convection but without conduction.

In some embodiments of the present invention, system 124 comprises a resistive heating element 128. When resistive heating is employed, heating system 124 is preferably position below device 10 and in thermal communication therewith. Preferably, heating system 124 comprises a stage 126 configured to automatically engage cartridge device 10 from below once cartridge device 10 is its place. This can be done in more than one way.

Figure 5B:
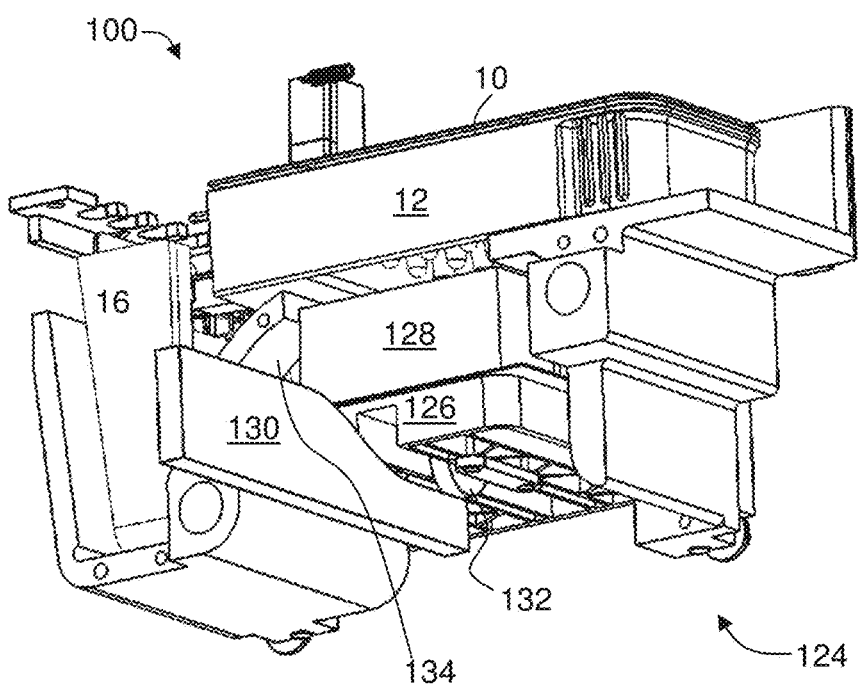
Figure 5C:
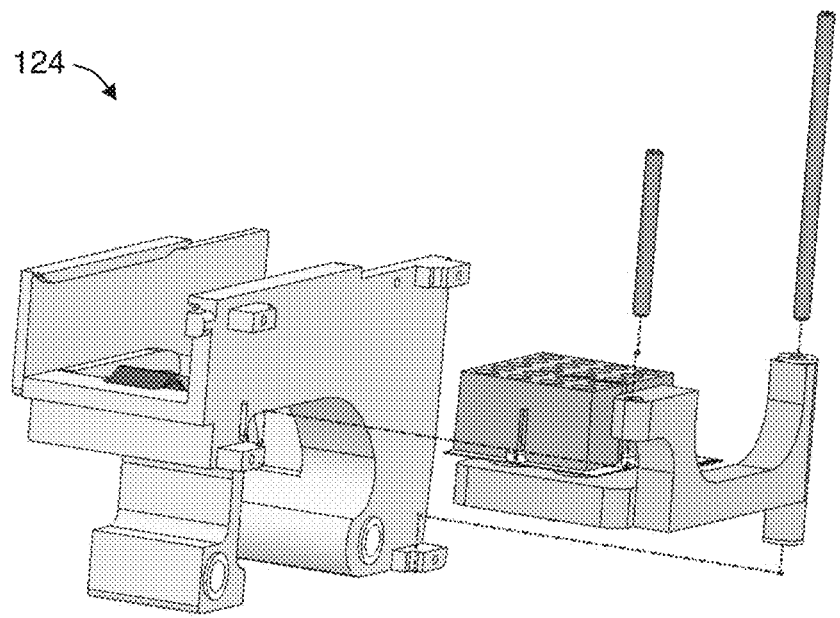
Figure 5D:
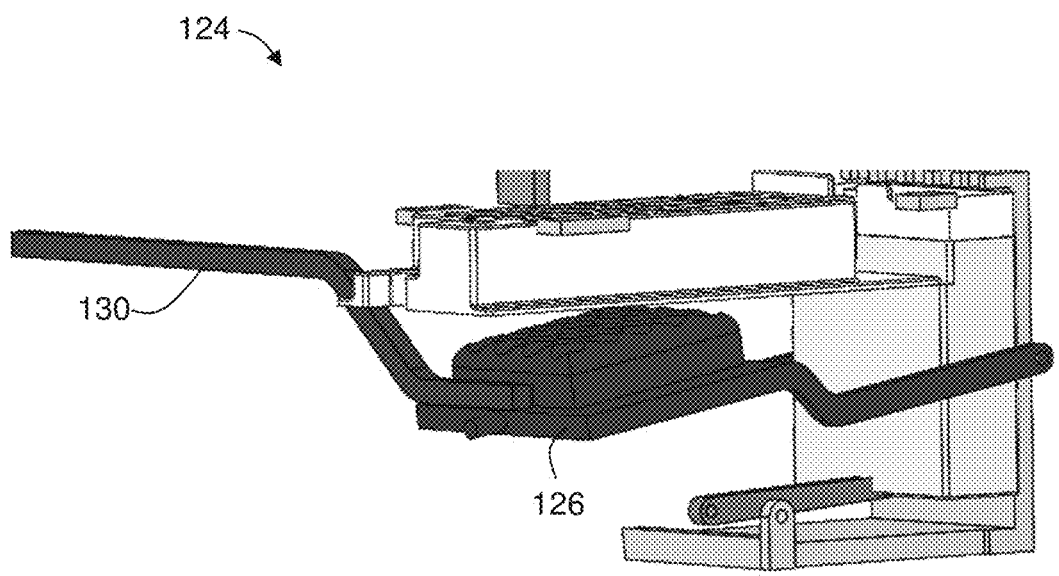

For example, in one embodiment, illustrated in FIGS. 5B-C, a cam 130 and a roller 132 are employed to raise heating element 128. In these embodiments, heating system 124 can also facilitates the alignment of cartridge device 10, in which case cam 130 also engages a datum feature 134 into member 16 for better alignment. FIG. 5C illustrates an exploded view of heating system 124.

Figure 5E:
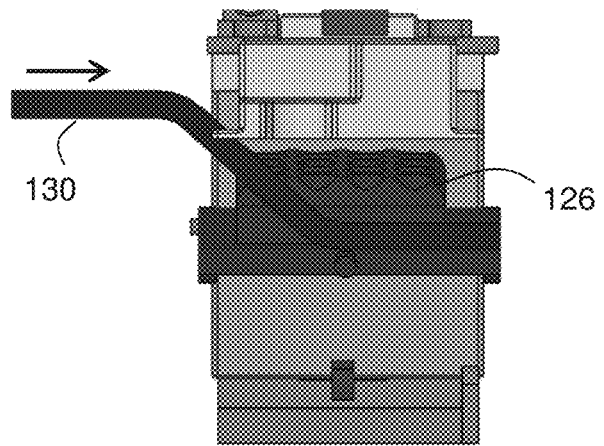
FIGS. 5E-G are schematic illustrations showing positions of a stage of heating system before (FIG. 5E), during (FIG. 5F) and after (FIG. 5G) a motion of a cam within the system shown in FIG. 4.
Figure 5F:
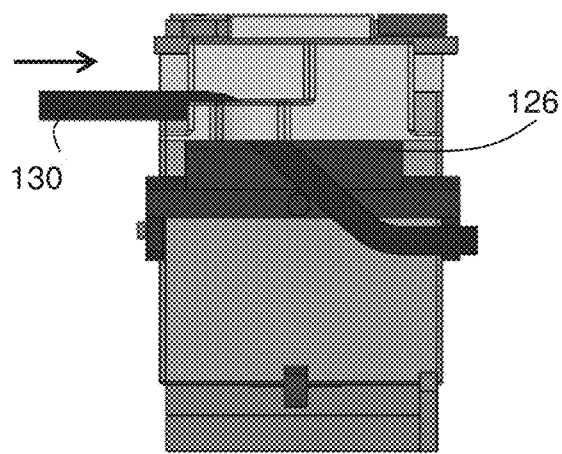
Figure 5G:
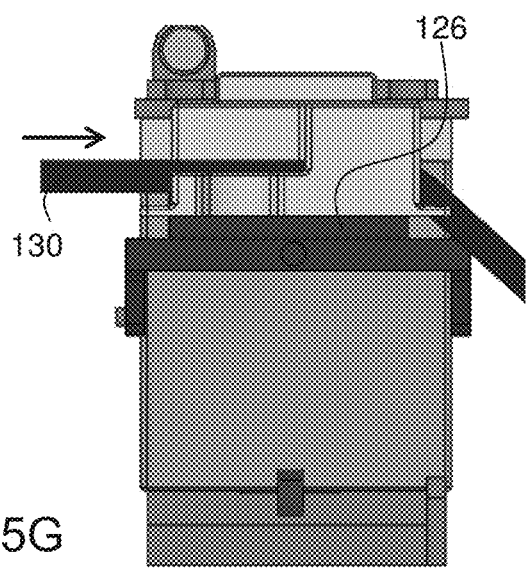

In other embodiments, illustrated in FIGS. 5D-G, stage 126 is biased upwards by a spring (not shown) but is held at a lower position by cam 130. Once cartridge device 10 is received, cam 130 is pushed by device 10 and releases stage 126 to move upwards. FIGS. 5E-G illustrate the position of stage 126 before (FIG. 5E), during (FIG. 5F) and after the completion (FIG. 5G) of the motion of cam 130.

Figure 6A:
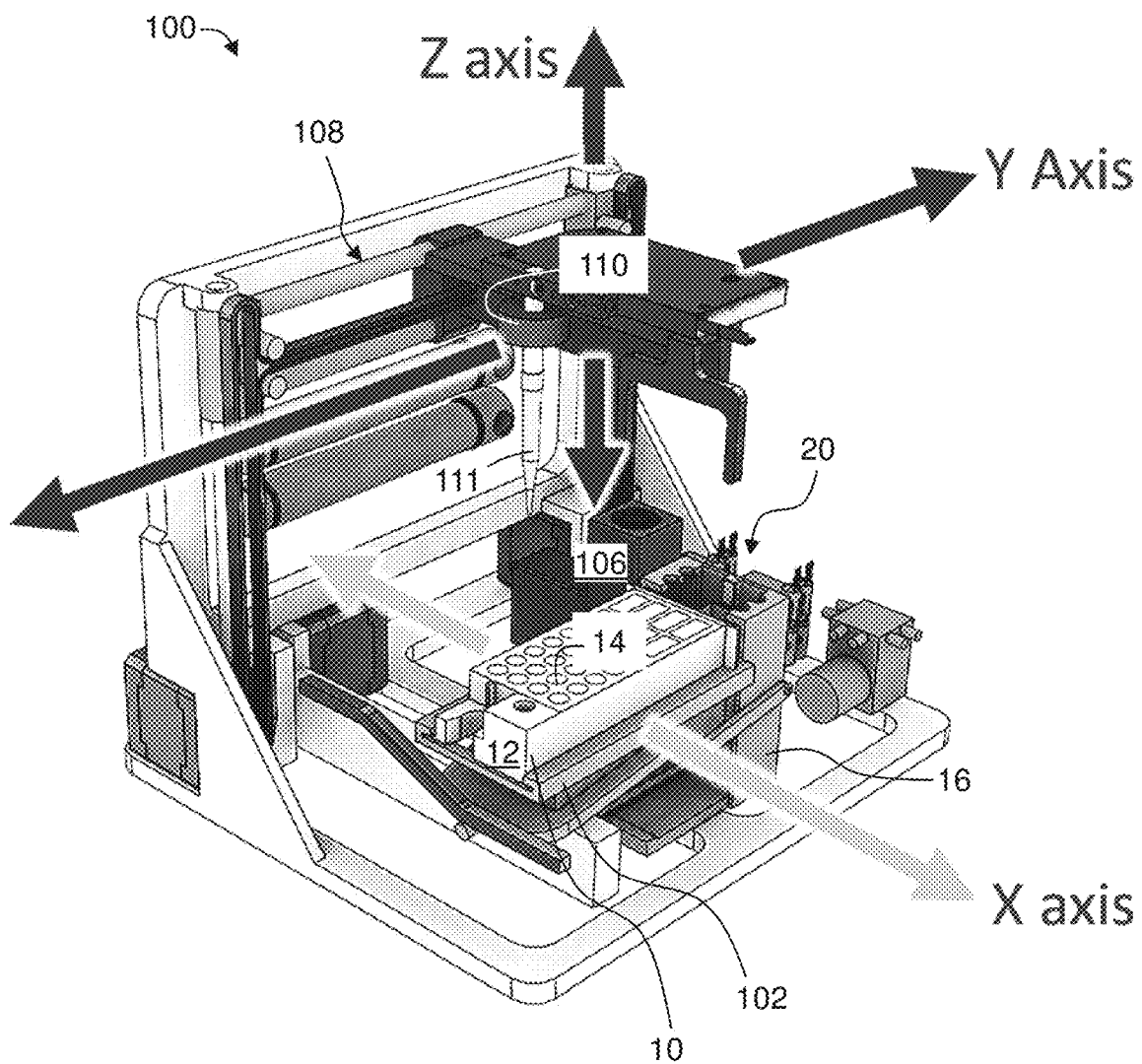
FIGS. 6A-C are schematic illustrations of a robotic arm system according to some embodiments of the present invention.
Figure 6B:
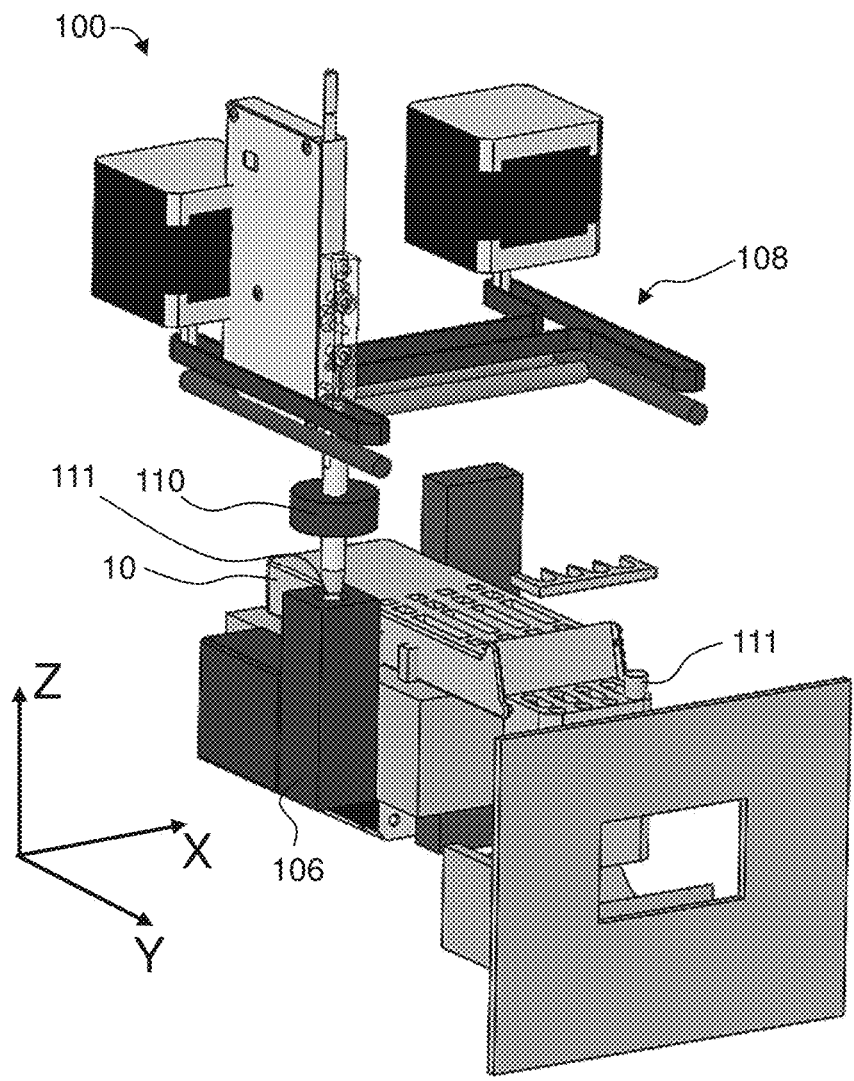
Figure 6C:
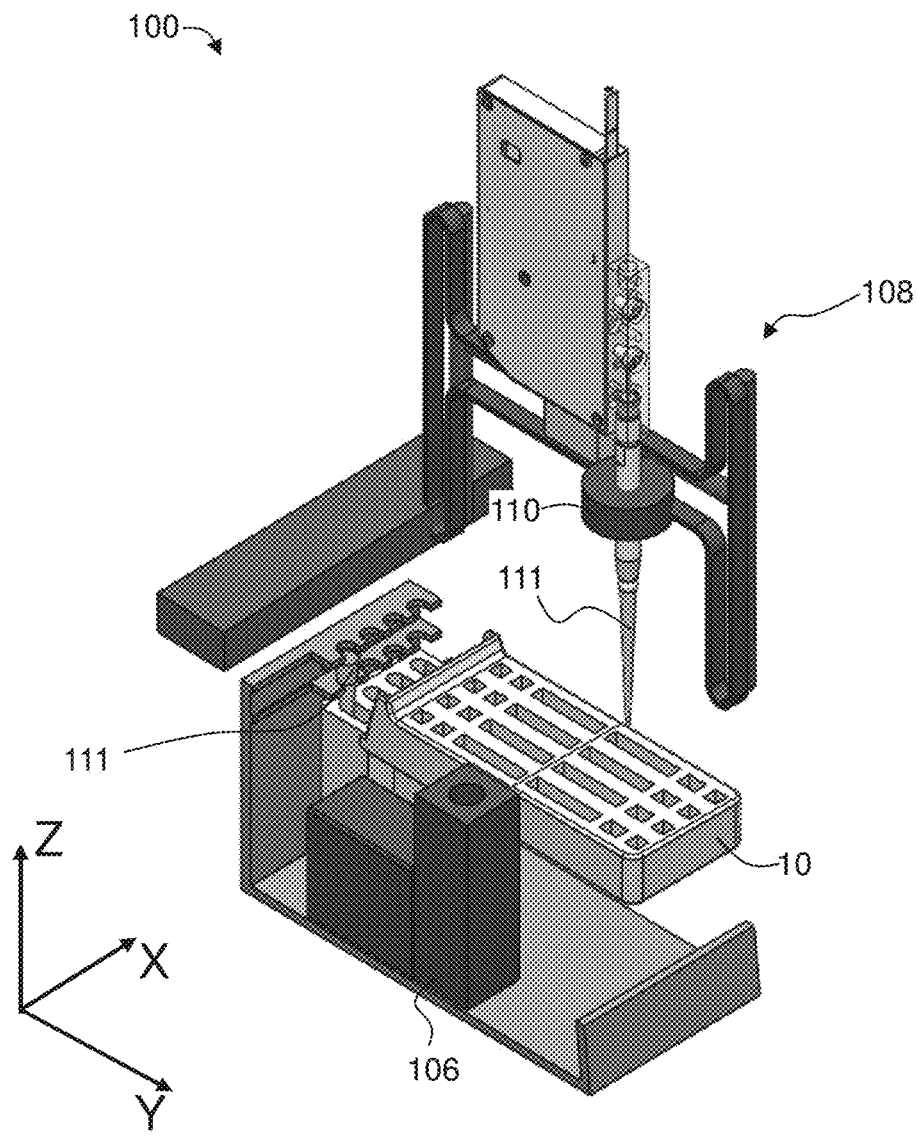

An additional partial laid-open view of system 100, illustrating robotic arm system 108 according to some embodiments of the present invention is provided in FIGS. 6A-C. Shown are three orthogonal Cartesian axes X, Y and Z of motion, where Z is along the vertical direction. In some embodiments of the present invention robotic arm system 108 is configured to move pipette 110 along a planar path in the Y-Z plane, and to move holder 102 linearly, and optionally reciprocally, along the X axis. These embodiments are illustrated in FIGS. 6A and 6B. In alternative embodiments of the present invention, robotic arm system 108 is configured to move pipette 110 along a planar path in the X-Z plane, and to move holder 102 linearly, and optionally reciprocally, along the Y axis. These embodiments are illustrated in FIG. 6C. In any event, the motion of robotic arm system 108 is preferably selected to allow tip 111 of pipette 110 to visit each of wells 14 of device 10, to visit compartment 20 of member 16, to visit analysis chamber 106, and to visit at least one of container 40 (when loaded into cavity 32 of device 10) and chamber 30 (when containing the liquid). When compartment 20 is partitioned into partitions 28, controller 112 is preferably configured for controlling robotic arm system 108 to pick up different pipette tips from different partitions and to correspondingly release different pipette tips into different partitions.

In embodiments in which cartridge device 10 comprises a waste collecting chamber 24, controller 112 of system 100 is preferably configured for controlling robotic arm system 108 to visit also waste collecting chamber 24, after visiting analysis chamber 106. In embodiments in which container 40 is placed in cavity 32 of cartridge device 10, controller 112 is configured for controlling robotic arm system 108 to visit container 40. When container 40 and/or cartridge device 10 comprises a pierceable film, controller 112 is preferably configured for controlling robotic arm system 108 to pierce the film by tip 111 of pipette 110.

Figure 7:
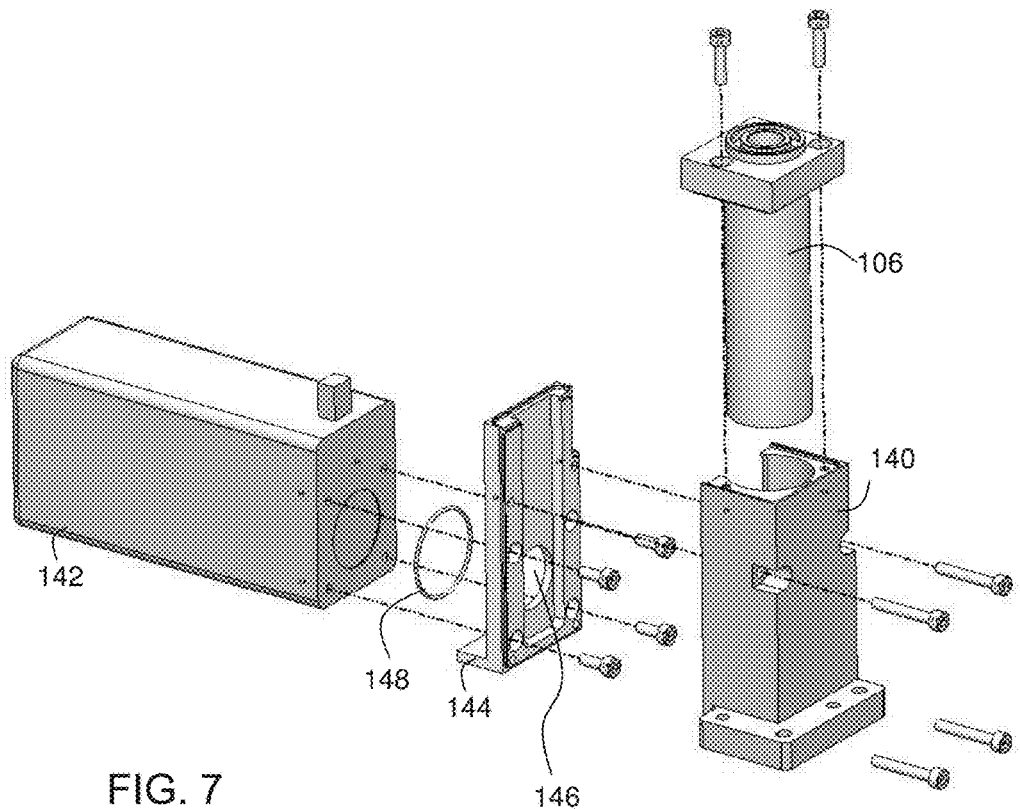
FIG. 7 is a schematic illustration showing an exploded view of an internal analyzer system, according to some embodiments of the present invention.

FIG. 7 is a schematic illustration showing an exploded view of internal analyzer system 104, according to some embodiments of the present invention. Preferably, analysis chamber 106 is a dark chamber and internal analyzer system 104 is an optical analyzer configured for detecting chemiluminescent signals from the pipette tip 111 (not shown in FIG. 7) when the pipette tip is in dark chamber 106. In the illustrated embodiment, dark chamber 106 is tubular and is held by a tube holder 140. An optical detector 142 such as, but not limited to, a photomultiplier tube (PMT) is mounted on a side wall of camber 106 by means of a mount structure 144 having an opening 146 for optical signal to propagate from chamber 106 through opening 146 and into optical detector 142. A sealing ring 148 is optionally and preferably introduced at opening 146 for preventing stray light from entering optical detector 142.

Figures 8A, 8B, 8C:
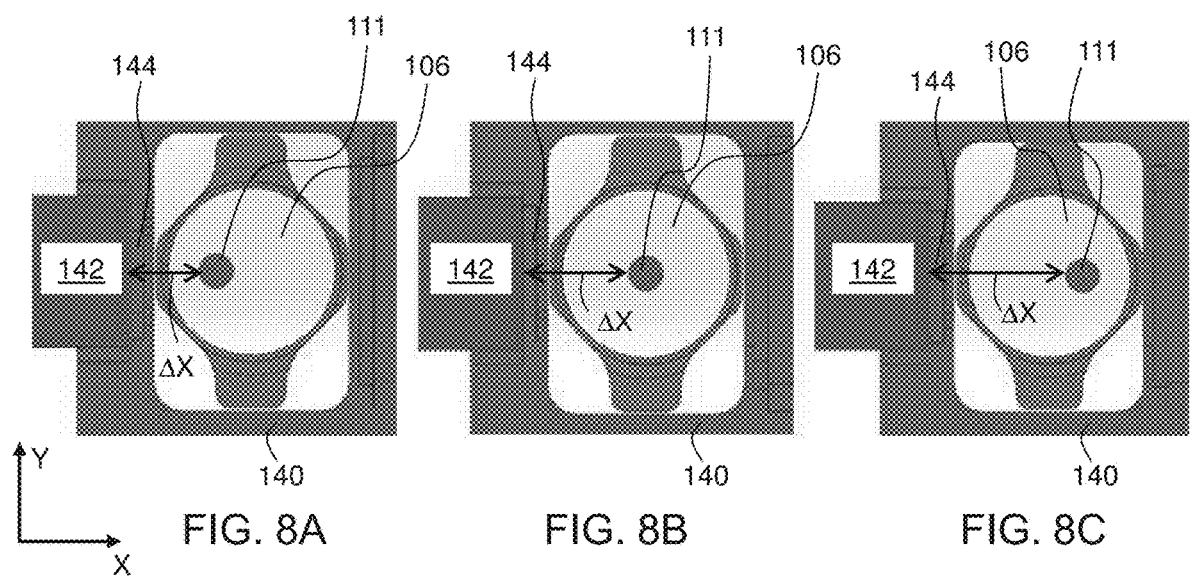
FIGS. 8A-C are schematic illustrations of a cross-section along a horizontal plane of the internal analyzer system, according to some embodiments of the present invention.

It was found by the inventors that the detection sensitivity varies with the variation of the position of the tip of the pipette within chamber 106, and particularly variations in the distance of the tip from the optical detector 142. FIGS. 8A-C are schematic illustrations of a cross-section along a horizontal plane of internal analyzer system 104, once assembled. Also shown, are three different horizontal positions of the tip 111 of pipette 110 once introduced into chamber 106. The distance between the tip 111 of pipette 110 and optical detector 142 is marked in FIGS. 8A-C by $\Delta X$. FIGS. 8A-C correspond to three different values of $\Delta X$, e.g., about 5 mm in FIG. 8A, about 10 mm in FIG. 8B, and about 15 mm in FIG. 8C.

Figure 9:
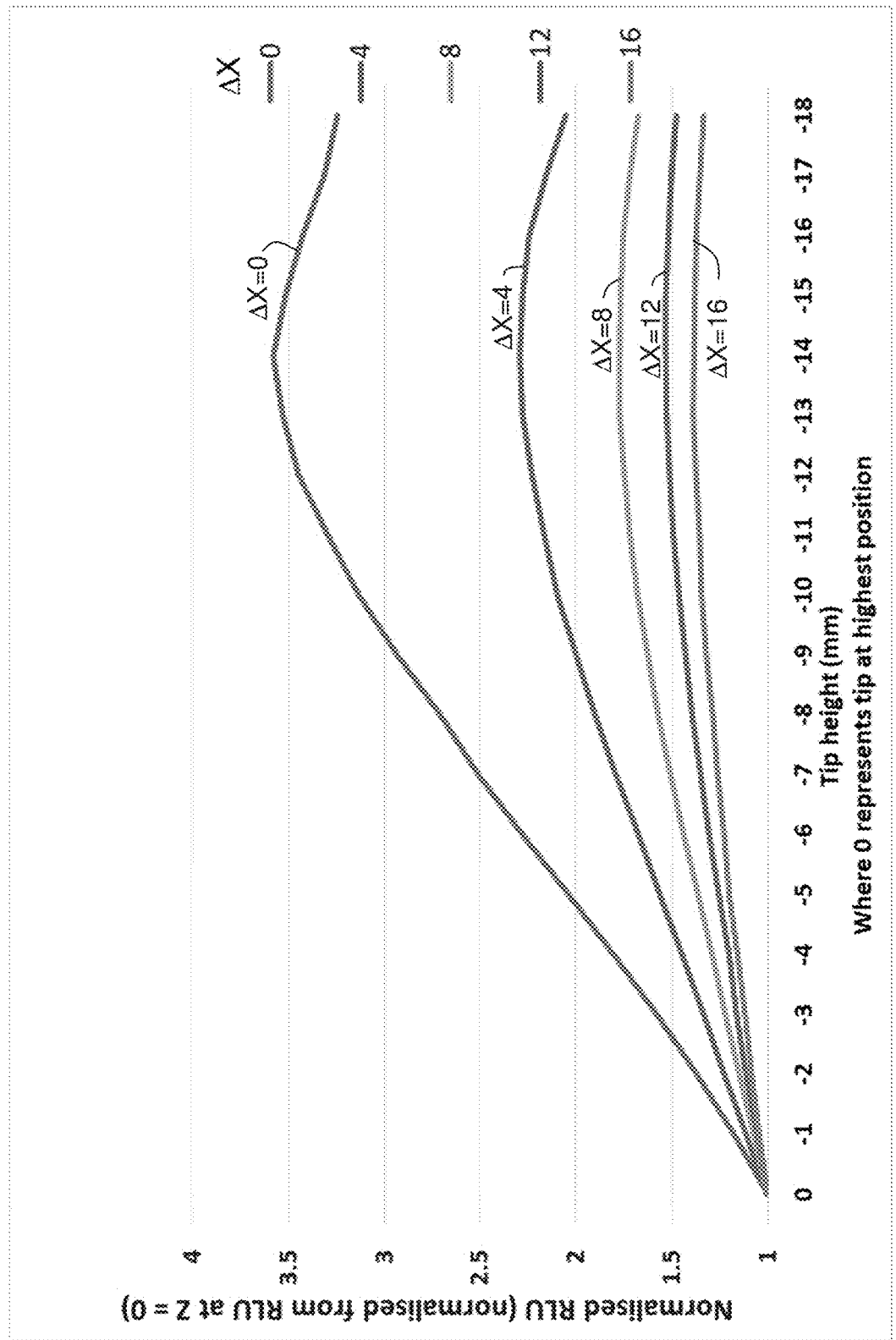
FIG. 9 is a graph showing an optical signal detected from a pipette tip as the pipette tip moves vertically at a constant horizontal position, as obtained in experiments performed according to some embodiments of the present invention.

FIG. 9 is a graph showing the detected optical signal as the pipette tip moves vertically (along the Z direction) at a constant horizontal position, as obtained in experiments performed according to some embodiments of the present invention using a PMT purchased from Hamamatsu Photonics K.K. Each curve in FIG. 9 corresponds to a different (constant) value of $\Delta X$, where the actual distance from the sensor in the optical detector is about 8+ΔX mm. A maximum attenuation of about 3.5 was observed. For a PMT purchased from ET Enterprises Ltd., smaller attenuation of 1.8 was observed since the detection window of Hamamatsu PMT is smaller than that on the ET PMT. As demonstrated in FIG. 9, the vertical position of the tip has a lesser impact than the horizontal position. The present Inventors also found that the detection is less sensitive to variations of the tip's horizontal position along the Y axis (perpendicularly to the optical axis of optical detector 142).

The present inventors found that when the internal walls of chamber 106 are coated, at least partially, by a reflective coating, the sensitivity to the variation in the horizontal distance between the tip and the optical detector is reduced.

The reflective coating can be, for example, an aluminum foil (optionally and preferably its matt side), a paper reflective coating, a metallic reflective coating. The reflective coating may be deposed onto the inner wall of chamber 106 by any technique known in the art including, without limitation, thermal disposition or vapor disposition, plating and the like. The reflective coating can also be in the form of a foil or leaf. The reflective coating may optionally and preferably be polished after application, or may be applied in a manner that produces a high degree of reflection without the need for polishing. A protective layer may optionally and preferably be formed or deposited to overly the reflective coating. For example, a protective oxide dielectric coating may be formed, for example using techniques commonly employed to form passivation layers in silicon fabrication processes. The oxide may provide environmental protection to the underlying reflective coating. The oxide may additionally or alternatively serve as a filter, ensuring reflection of certain defined wavelengths or ranges of wavelengths, while reducing or eliminating the reflection of other wavelengths or ranges of wavelengths. Thus, wavelengths which are not of interest may be advantageously suppressed.

Figure 10:
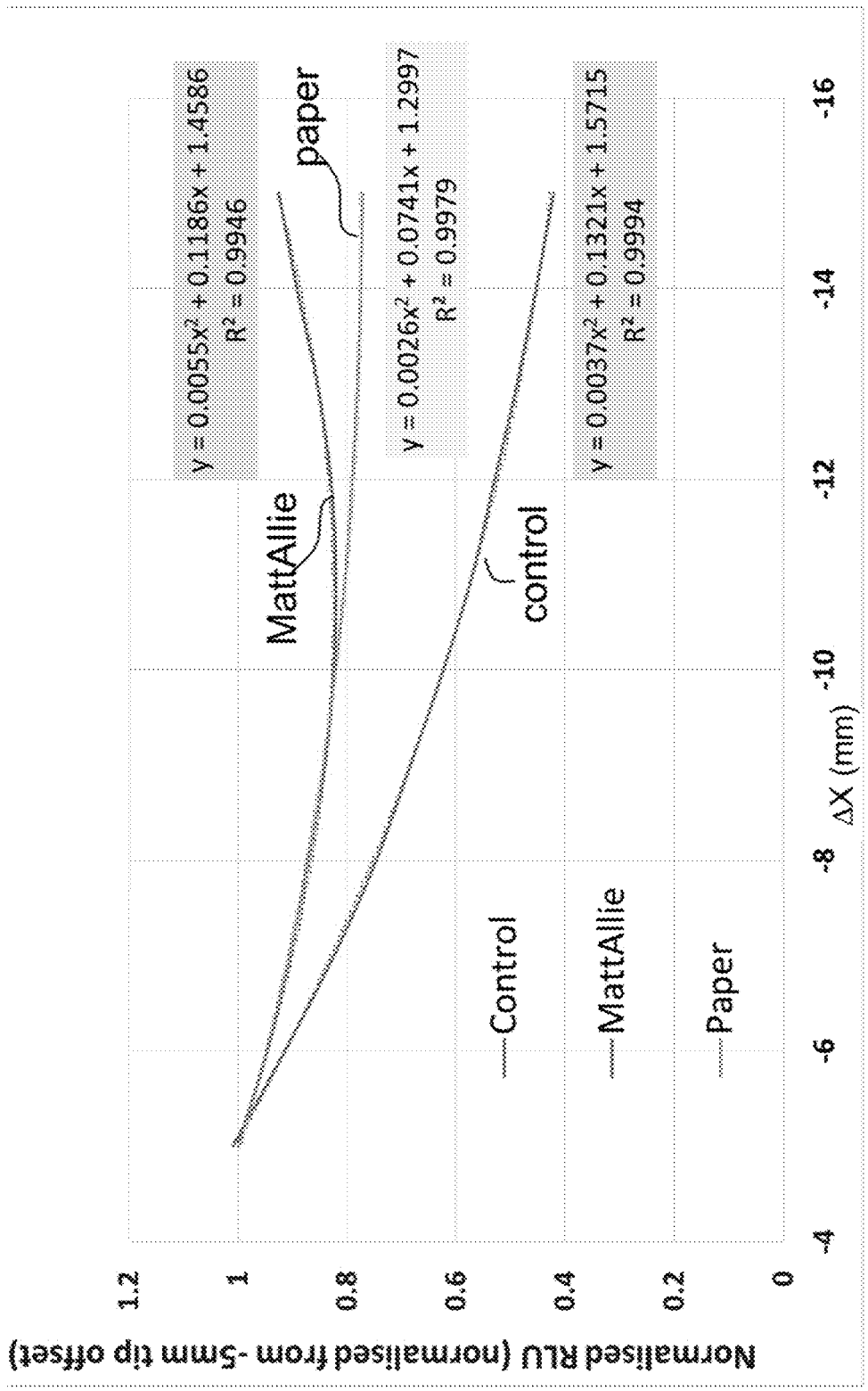
FIG. 10 is a graph showing a depended of an intensity decay on a horizontal location of the pipette tip, as obtained during experiments performed according to some embodiments of the present invention.

FIG. 10 is a graph showing an intensity decay as a function of ΔX, where the actual distance from the sensor in the optical detector is about 8+ΔX mm, as obtained during experiments performed according to some embodiments of the present invention using a matt side of an aluminum foil (designated "MattAllie" in FIG. 10) reflective coating, a paper reflective coating, and no reflective coating (control). As shown the intensity curves are considerably shallower with the reflective coating than without the reflective coating. Since the sensitivity is directly proportional to the gradient of these curves, FIG. 10 demonstrates that the use of reflective coating reduces the positional accuracy required the robotic arm system 108.

While the dark chamber 106 can have any shape or form, certain shapes that enhance reflection toward the optical detector 142 are preferred. Preferably, an interior of the dark chamber 106 has a physical form capable of reflecting or otherwise directing at least a portion of the photons generated by the reaction within the pipette tip towards optical detector 142. Such reflection can be accomplished using one or more concave inner surfaces as the internal wall of the dark chamber 106. In at least some instances, the concave inner surface can be generally oval or cylindrical, for example as shown in FIG. 7. Also contemplated are embodiments in which the inner wall of dark chamber 106 are generally spherical or hemispherical.

Figure 11A:
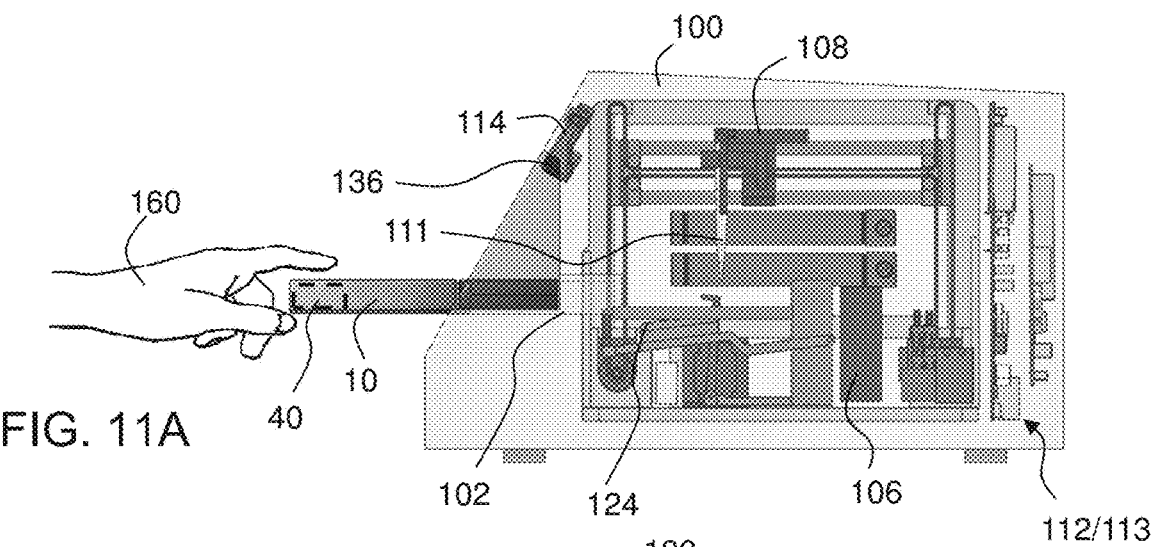
FIGS. 11A-C are schematic illustrations of an operation procedure of the system shown in FIG. 4, according to some embodiments of the present invention.
Figure 11B:
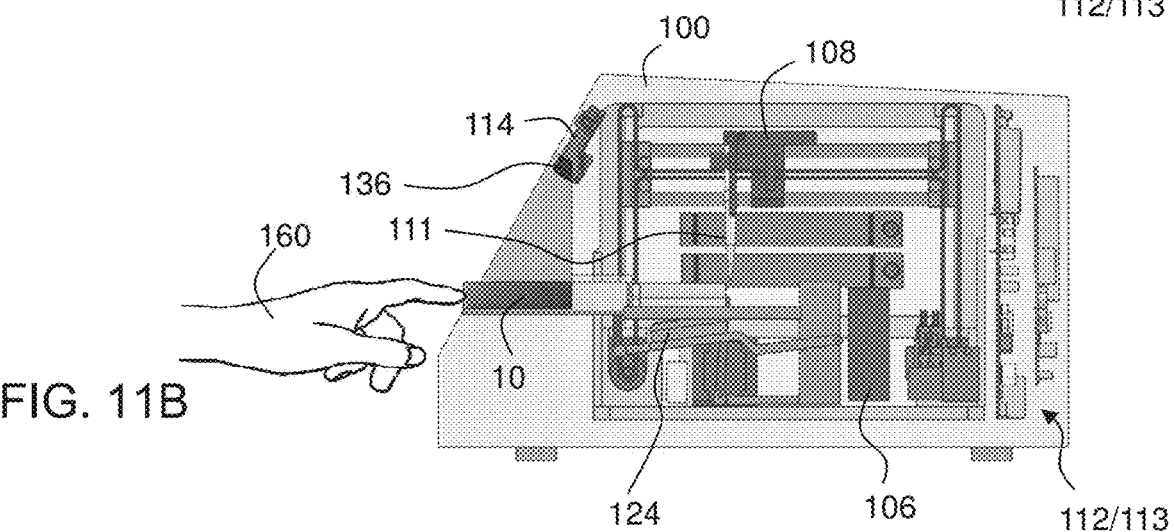
Figure 11C:
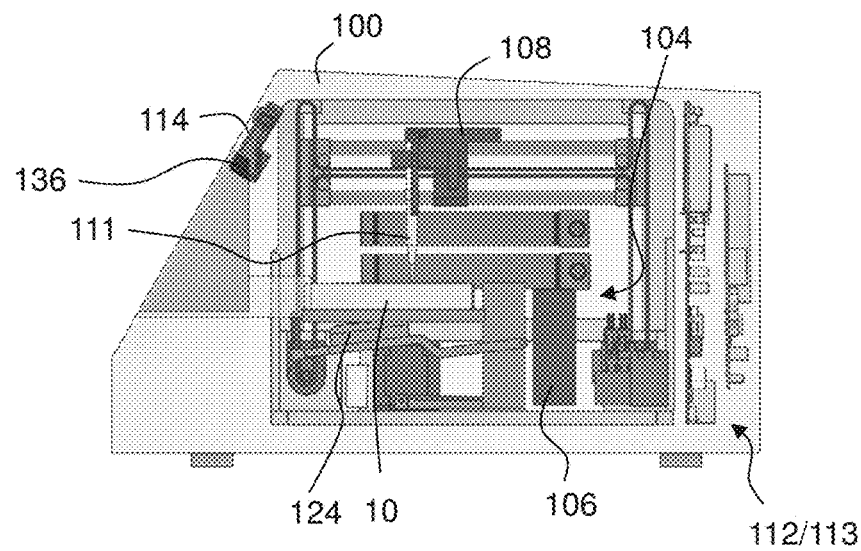

A representative operation procedure of system 100 will now be described with reference to FIGS. 11A-C. Cartridge device 10, with wells filled with substances for performing the assay, with sterile disposable tips placed within compartment 20 of hinged second member 16, and with container 40 placed within cavity 32, is introduced by the operator 160 to holder 102 (FIG. 11A), wherein container 40 already contains the liquid (e.g., body liquid). Alternatively, instead of container 40 within cavity 32, chamber 30 can include a liquid (e.g., body liquid) as further detailed hereinabove. Still alternatively, device 10 can be loaded with two types of liquids one type in container 40 and another type in chamber 30. A non-limiting example includes a scenario in which a capillary blood sample is introduced into container 40 which is then loaded into cavity 32 of device 10 to allow measurements of host (patient) proteins, and a nasal mucus sample (collected by a nasal swab) is introduced into chamber 30 of the same device 10 to allow measurements of presence, absence or level of micro-organism (e.g., bacteria, virus, fungi) related proteins, for example hemagglutinin and neuraminidase of the influenza virus. In this specific exemplary embodiment, device 10 is used to monitor both the host response to a potential infection and to detect or quantify the presence of a disease causing agent. The wells can contain an antibody that is immobilized to the solid magnetic carrier, a labeled antibody, and a wash buffer.

Cartridge device 10 is then pushed forward into system 100 (FIG. 11B), optionally and preferably until an acoustic indication (e.g., a click) or mechanical detent is effected to indicate that the cartridge device 10 is properly inserted. Lever system 116 (not shown, see FIG. 5A) draws cartridge device 10 further inwards and hinges the second member 16 (not shown in FIGS. 11A-C, see FIGS. 5A-B) of device 10. Heating system 124 engages the bottom of device 10 as further detailed hereinabove.

Optionally, the robotic arm picks up one of tips from the tip container by way of driving the robotic arm mandrel into one of the tips in the container, which causes the tip to expand and attach to the robotic arm by friction. The robotic arm then maneuvers the tip such that it leaved container without any obstacles.

Optionally, the information on identifier 34 (not shown) is read by reader 136. Controller 112 establishes a relative motion between device 10 and pipette 110 such that pipette 110 visits compartment 20 and connects to one of the new tips in compartment 20 (not shown in FIGS. 11A-C, see FIGS. 1A, 1B, 1D, 5A and 5B). Controller 112 then establishes a relative motion between device 10 and pipette 110 such that pipette 110 aspirates into tip 111 the liquid (either from container 40 or from chamber 30), as well as the antibody that is immobilized to the solid magnetic carrier, by visiting container 40 or chamber 30 and the respective wells. Controller 112 also ensure that pipette 110 aspirates into tip 111 the wash buffer from the respective well, and moves the pipette 110 such that tip 111 is proximate to magnet 150 (not shown, see FIG. 4). The magnetic field generated by magnet 150 separates the solid magnetic carrier thereby also the target substance from other components in tip 111 of pipette 110, wherein the solid magnetic carrier is concentrated at the side wall of tip 111 of pipette 110. While the solid magnetic carrier is at the side wall, controller 112 causes pipette 110 to release into the waste collection chamber of device 10 the wash buffer from tip 111, including any component that is not immobilized to the magnetic carrier.

According to some embodiments of the invention, two magnets can be used to achieve the separation of the target substance from other materials. One magnet can be used to attract the solid carrier into the tip wall, and another magnet can then be employed to change the magnetic field such that when the pipette is releasing the waste material, the target substance is retained with greater efficacy than achievable with the magnetic field used for attracting the solid carrier.

Controller 112 then causes pipette 110 to aspirate into tip 111 the labeled antibody from the respective well. The labeled antibody binds to the target substance on the magnetic carrier. Controller 112 can then optionally and preferably move tip 111 of pipette 110 into a well that contains inhibitory solution, for contacting the outer walls of tip 111 by the inhibitory solution. Preferably, the inhibitory solution does not enter the tip. This can be ensured by not operating pipette 110 to aspirate the inhibitory solution into tip 111.

Controller 112 moves tip 111 of pipette 110 into chamber 106 for analysis by internal analyzer system 104, which optionally and preferably uses processor 113 for the analysis. For example, processor 113 can receive signals from the optical detector of system 104 and determine the existence, absence, or level of the target substance in the liquid (e.g., body liquid) based on the intensity of the signals.

When the outer walls of tip 111 is contacted with the inhibitory solution, of tip 111 preferably enters into chamber 106 immediately after said contact. It was surprisingly found by the Inventors that such a procedure significantly reduces the possibility of non-specific enzyme activity.

Once the analysis is completed, controller 112 establishes a relative motion between device 10 and pipette 110 until tip 111 of pipette 110 enters compartment 20 of hinged second member 16 (not shown in FIGS. 11A-C, see FIGS. 1A, 1D, 5A and 5B) of device 10. Controller 112 releases tip 111 of pipette 110 into compartment 20.

Optionally in some embodiments of the invention, the tip is released by the way of the robot, after having placed tip in the designated location within compartment 20, then moves up through either a fixed or moving mechanical fork-like structure which is narrower than the width of the tip, but wider than the width of the robotic arm mandrel. The tip is then forced away from the mandrel, and the tip is then released when the robotic arm continues the motion through the mechanical fork-like structure.

Optionally and preferably, controller 112 causes robotic arm 108 to pick up another new pipette tip from compartment 20 and performs another assay by repeating the above operations protocol with another set of wells of the same cartridge. Processor 113 can instruct the display 114 to display the results obtained from one or more of the performed assays.

Optionally and preferably, the system has a door mechanism, which is opened when a cartridge needs to be loaded into the system, and when a cartridge is ejected from the device. In all other times, the door is closed which prevents operators' access to the internal components of the analyzer.

In some embodiments of the present invention device 10 and system 100 are subjected to a calibration and testing procedure. A calibrating liquid and auxiliary liquids for testing the cartridge device 10 and system 100 are stored in a dropper and put into the cartridge device 10 with drops to circumvent use of pipette. Vials with calibrating liquids can be stored within a vial with a nozzle. The operator can tip the vial nozzle into the sample chamber 30, and apply a predetermined number of drops into sample chamber 30. The inventors found that this reduces the possibility of bubble formation when dispensing the calibrator fluid into the sample well.

According to some embodiments of system 100 has dimensions of Xcm×Ycm×Zcm, wherein each of X, Y and Z is from about 75 to about 125, e.g., about 100. According to some embodiments of the system has dimensions of Xcm×Ycm×Zcm, wherein each of X, Y and Z is from about 35 to about 65, e.g., about 50. According to some embodiments of the system has dimensions of Xcm×Ycm×Zcm, wherein each of X, Y and Z is from about 16 to about 30, e.g., about 23. According to some embodiments of the system has dimensions of Xcm×Ycm×Zcm, wherein each of X and Y is from about 20 to about 26, e.g., about 23, and wherein Z is from about 26 to about 34, e.g., about 30.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

ANNEX

It will be appreciated that the protein names presented herein are given by way of example. Many alternative names, aliases, modifications, isoforms and variations will be apparent to those skilled in the art. Accordingly, it is intended to embrace all the alternative protein names, aliases, modifications isoforms and variations.

Gene products, are identified based on the official letter abbreviation or gene symbol assigned by the international Human Genome Organization Naming Committee (HGNC) and listed at the date of this filing at the US National Center for Biotechnology Information (NCBI) web site also known as Entrez Gene.

TRAIL: The protein, TNF Related Apoptosis Inducing Ligand (TRAIL), encoded by this gene is a cytokine that belongs to the tumor necrosis factor (TNF) ligand family. Additional names of the gene include without limitations APO2L, TNF-related apoptosis-inducing ligand, TNFSF10 and CD253. TRAIL exists in a membrane bound form and a soluble form, both of which can induce apoptosis in different cells, such as transformed tumor cells. This protein binds to several members of the TNF receptor superfamily such as TNFRSF10A/TRAILR1, NFRSF10B/TRAILR2, NFRSF10C/TRAILR3, TNFRSF10D/TRAILR4, and possibly also to NFRSF11B/OPG. The activity of this protein may be modulated by binding to the decoy receptors such as NFRSF10C/TRAILR3, TNFRSF10D/TRAILR4, and NFRSF11B/OPG that cannot induce apoptosis. The binding of this protein to its receptors has been shown to trigger the activation of MAPK8/JNK, caspase 8, and caspase 3. Alternatively spliced transcript variants encoding different isoforms have been found for this gene. TRAIL can be proteolytically cleaved from the cell surface to produce a soluble form that has a homotrimeric structure.

According to some embodiments, at least one of wells 14 contains an antibody that binds with the soluble (i.e. secreted) form of TRAIL.

According to some embodiments, at least one of wells 14 contains an antibody that binds with the membrane form of TRAIL is measured.

According to some embodiments, at least one of wells 14 contains an antibody that binds with the membrane form of TRAIL and at least one of wells 14 contains an antibody that binds with the secreted form of TRAIL.

IP10: This gene encodes a chemokine of the CXC subfamily and ligand for the receptor CXCR3. Binding of this protein to CXCR3 results in pleiotropic effects, including stimulation of monocytes, natural killer and T-cell migration, and modulation of adhesion molecule expression. Additional names of the gene include without limitations: IP-10, CXCL10, Gamma-IP10, INP10 and chemokine (C-X-C motif) ligand 10.

CRP: C-reactive protein; additional aliases of CRP include without limitation RP11-419N10.4 and PTX1. The protein encoded by this gene belongs to the pentaxin family. It is involved in several host defense related functions based on its ability to recognize foreign pathogens and damaged cells of the host and to initiate their elimination by interacting with humoral and cellular effector systems in the blood. Consequently, the level of this protein in plasma increases greatly during acute phase response to tissue injury, infection, or other inflammatory stimuli. CRP displays several functions associated with host defense: it promotes agglutination, bacterial capsular swelling, phagocytosis and complement fixation through its calcium-dependent binding to phosphorylcholine.

IL1RA: The protein encoded by this gene is a cytokine receptor that belongs to the interleukin 1 receptor family. This protein is a receptor for interleukin alpha (IL1A), interleukin beta (IL1B), and interleukin 1 receptor, type I (IL1R1/IL1RA). It is an important mediator involved in many cytokine induced immune and inflammatory responses. Additional names of the gene include without limitations: CD121A, IL-1RT1, p80, CD121a antigen, CD121A, IL1R and IL1ra.

PCT: Procalcitonin (PCT) is a peptide precursor of the hormone calcitonin, the latter being involved with calcium homeostasis. Procalcitonin ("pCT") is a protein consisting of 116 amino acids and having a molecular weight of about 13,000 dalton. It is the prohormone of calcitonin, which under normal metabolic conditions is produced and secreted by the C cells of the thyroid. pCT and calcitonin synthesis is initiated by translation of preprocalcitonin ("pre-pCT"), a precursor peptide comprising 141 amino acids. The amino acid sequence of human pre-pCT was described by Moullec et al. in FEBS Letters, 167:93-97 in 1984. pCT is formed after cleavage of the signal peptide (first 25 amino acids of pre-pCT).

SAA: encodes a member of the serum amyloid A family of apolipoproteins. The encoded protein is a major acute phase protein that is highly expressed in response to inflammation and tissue injury. This protein also plays an important role in HDL metabolism and cholesterol homeostasis. High levels of this protein are associated with chronic inflammatory diseases including atherosclerosis, rheumatoid arthritis, Alzheimer's disease and Crohn's disease. This protein may also be a potential biomarker for certain tumors. Alternate splicing results in multiple transcript variants that encode the same protein.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A cartridge device for analyzing a body liquid, the cartridge comprising:
   at least one disposable pipette tip;
   a first member having a plurality of wells for performing assays; and
   a second member, connected to said first member, and having a compartment holding said at least one disposable pipette tip;
   wherein said second member is hingedly connected to said first member in a manner that when said first member and said second member are held horizontally, said at least one disposable pipette tip is also horizontal, and when said hingedly connected second member is rotated downwards relative to said horizontally held first member, said compartment of said second member holds said at least one disposable pipette tip in a vertical orientation.

2. The device according claim 1, further comprising an openable or pierceable covering structure covering said plurality of wells.

3. The device according to claim 1, further comprising a waste collecting chamber.

4. The device according to claim 3 comprising a lid, wherein said waste collecting chamber is covered by said lid.

5. The device according to claim 3 comprising a lid, wherein said waste collecting chamber is covered by said lid and wherein said lid is connected to or is an extension of said second member, to be exposed when said horizontally held second member is rotated downwards relative to said horizontally held first member to a vertical orientation.

6. The device according to claim 1, wherein said second member is partitioned into a plurality of partitions, each constituted for holding one pipette tip.

7. The device according to claim 1, wherein said plurality of wells comprises at least one well containing a first antibody immobilized on a solid magnetic carrier, and at least one well containing a second antibody labeled with labeling substance, and wherein said antibodies are selected to specifically bind to a target substance in the body liquid.

8. The device according to claim 1, further comprising said at least one disposable pipette tip within said compartment.

9. The device according to claim 8, wherein said at least one disposable pipette tip comprises antibody immobilized to solid magnetic carriers in said at least one disposable pipette tip.

10. The device according to claim 1, wherein said first or second member comprises a cavity constituted for receiving and fittedly holding a container containing the body liquid.

\* \* \* \* \*